US012571742B2

(12) United States Patent
Sakai et al.

(10) Patent No.: US 12,571,742 B2
(45) Date of Patent: Mar. 10, 2026

(54) APPEARANCE INSPECTION DEVICE, WELDING SYSTEM, AND METHOD FOR APPEARANCE INSPECTION OF A WELD

(71) Applicant: Panasonic Intellectual Property Management Co., Ltd., Osaka (JP)

(72) Inventors: Toru Sakai, Hyogo (JP); Michio Sakurai, Osaka (JP); Daichi Higashi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 18/745,125

(22) Filed: Jun. 17, 2024

(65) Prior Publication Data

US 2024/0337608 A1     Oct. 10, 2024

Related U.S. Application Data

(63) Continuation of application No. PCT/JP2022/044533, filed on Dec. 2, 2022.

(30) Foreign Application Priority Data

Dec. 24, 2021    (JP) ................................. 2021-210114

(51) Int. Cl.
   *G01N 21/95*      (2006.01)
   *G01N 21/88*      (2006.01)
       (Continued)

(52) U.S. Cl.
   CPC ..... *G01N 21/9515* (2013.01); *G01N 21/8851* (2013.01); *G01N 33/207* (2019.01);
       (Continued)

(58) Field of Classification Search
None
See application file for complete search history.

(56) References Cited

U.S. PATENT DOCUMENTS 11,904,417 B2 * 2/2024 Monjardin ............... B23K 9/18
12,330,241 B1 * 6/2025 Yin ........................ B23K 31/00
(Continued)

FOREIGN PATENT DOCUMENTS

EP         3900870        10/2021
JP      2017-148878       8/2017
(Continued)

OTHER PUBLICATIONS

Yang, L., Fan, J., Huo, B et al. Inspection of Welding Defect Based on Multi-feature Fusion and a Convolutional Network. J Nondestruct Eval 40, 90 (2021). (Year: 2021).*

(Continued)

*Primary Examiner* — Stefan Gadomski
(74) *Attorney, Agent, or Firm* — Wenderoth, Lind & Ponack, L.L.P.

(57) ABSTRACT

An appearance inspection apparatus includes a shape measurement unit configured to measure the three-dimensional shape of a weld and a data processor configured to process sample shape data and shape data acquired by the shape measurement unit. The data processor includes a first learning data set generator configured to generate a plurality of first learning data sets based on the sample shape data, a second learning data set generator configured to generate a plurality of second learning data sets based on the first learning data sets, a determination model generator configured to generate multiple types of determination models using the second learning data sets, and a first determination (Continued)

unit configured to determine whether the shape of the weld is good or bad based on the shape data and one of the determination models.

18 Claims, 22 Drawing Sheets

(51) Int. Cl.
 *G01N 33/207* (2019.01)
 *G06T 7/00* (2017.01)
(52) U.S. Cl.
 CPC ...... *G06T 7/0004* (2013.01); *G01N 2201/101* (2013.01); *G06T 2207/20081* (2013.01); *G06T 2207/30136* (2013.01)

(56) References Cited

U.S. PATENT DOCUMENTS

| | | | | |
|---|---|---|---|---|
| 2010/0314362 | A1* | 12/2010 | Albrecht | B23K 37/00 |
| | | | | 219/121.63 |
| 2015/0060424 | A1* | 3/2015 | Daniel | B23K 31/12 |
| | | | | 219/130.21 |
| 2016/0193681 | A1* | 7/2016 | Pesme | B23K 9/1274 |
| | | | | 219/136 |
| 2016/0288236 | A1* | 10/2016 | Becker | B23K 9/0956 |
| 2017/0032281 | A1* | 2/2017 | Hsu | G06Q 10/06 |
| 2018/0250763 | A1* | 9/2018 | Kita | B23K 9/1006 |
| 2020/0061753 | A1 | 2/2020 | Izumi | |
| 2020/0406392 | A1 | 12/2020 | Fukushima et al. | |
| 2021/0037196 | A1* | 2/2021 | McGovern | G01N 21/3563 |
| 2021/0308782 | A1 | 10/2021 | Sakurai et al. | |
| 2021/0316403 | A1* | 10/2021 | Dariol | B23K 31/006 |
| 2021/0318673 | A1* | 10/2021 | Kitchen | G05B 13/048 |
| 2022/0011240 | A1* | 1/2022 | Schwarz | B23K 26/38 |
| 2022/0134464 | A1* | 5/2022 | Jiao | B23K 9/02 |
| | | | | 219/124.34 |
| 2022/0152720 | A1* | 5/2022 | Hazui | B23K 9/167 |
| 2022/0161344 | A1* | 5/2022 | Zhang | B23K 31/125 |
| 2022/0230301 | A1* | 7/2022 | Thomasset | G06T 7/0004 |
| 2022/0297218 | A1* | 9/2022 | Yashima | B23K 9/0953 |
| 2023/0129188 | A1* | 4/2023 | Hsu | B23K 31/125 |
| | | | | 706/12 |
| 2023/0137232 | A1* | 5/2023 | Goya | G05B 19/4184 |
| | | | | 73/865.9 |
| 2023/0221286 | A1* | 7/2023 | Wada | G06T 7/001 |
| | | | | 382/141 |
| 2023/0241703 | A1* | 8/2023 | Furukawa | B23K 9/0953 |
| | | | | 219/130.21 |
| 2023/0264285 | A1* | 8/2023 | Ozaki | B23K 31/006 |
| | | | | 219/137 R |
| 2023/0330784 | A1* | 10/2023 | Asai | B25J 13/087 |
| 2024/0227086 | A1* | 7/2024 | Zhang | B23K 31/125 |
| 2024/0316670 | A1* | 9/2024 | Kashanipour | B23K 9/0953 |
| 2024/0337608 | A1* | 10/2024 | Sakai | G06N 20/00 |
| 2025/0073825 | A1* | 3/2025 | Vithanage | G01N 29/228 |
| 2025/0091151 | A1* | 3/2025 | Miwa | B23K 9/12 |
| 2025/0191129 | A1* | 6/2025 | Goto | G06T 5/50 |
| 2025/0231102 | A1* | 7/2025 | Kim | G01N 33/2045 |

FOREIGN PATENT DOCUMENTS

| | | |
|---|---|---|
| JP | 2019-188435 | 10/2019 |
| JP | 2020-28909 | 2/2020 |
| JP | 2021-007957 | 1/2021 |
| JP | 2021-171810 | 11/2021 |
| WO | 2020/129617 | 6/2020 |
| WO | 2020/129618 | 6/2020 |

OTHER PUBLICATIONS

International Search Report issued in International Application PCT/JP2022/044533 on Feb. 21, 2023.

\* cited by examiner

SCANNING DIRECTION

21

21b

21a

EMITTED LIGHT

REFLECTED LIGHT

200

201

Z

Y

X

22

22a

SHAPE
MEASUREMENT UNIT

DATA PROCESSOR

CPU

RAM

SAMPLE SHAPE DATA

DATA AUGMENTATION ⇒ FIRST LEARNING DATA SET

SAMPLE SHAPE DATA                    DATA AUGMENTATION ⇒ FIRST LEARNING DATA SET

SAMPLE SHAPE DATA             DATA AUGMENTATION ⇒ FIRST LEARNING DATA SET

Y-DIRECTION RESOLUTION

AFTER CHANGING RESOLUTION

Y

X

201

Y-DIRECTION RESOLUTION

BEFORE CHANGING RESOLUTION

BEFORE CHANGING DATA DENSITY
(BEFORE THINNING)

AFTER CHANGING DATA DENSITY
(AFTER THINNING)

AFTER CHANGING DATA DENSITY
(AFTER THINNING)

204

BEFORE CHANGING DATA DENSITY
(BEFORE THINNING)

APPEARANCE INSPECTION DEVICE, WELDING SYSTEM, AND METHOD FOR APPEARANCE INSPECTION OF A WELD

CROSS-REFERENCE TO RELATED APPLICATIONS

This is a continuation of International Application No. PCT/JP2022/044533 filed on Dec. 2, 2022 which claims priority to Japanese Patent Application No. 2021-210114 filed on Dec. 24, 2021. The entire disclosures of these applications are incorporated by reference herein.

BACKGROUND

The present disclosure relates to an appearance inspection device, a welding system, and a method for appearance inspection of a weld.

Inspecting the appearance of a weld using determination models reinforced by machine learning to determine whether the shape of the weld is good or bad has recently become popular.

For example, International Patent Publication No. WO 2020/129617 proposes a weld appearance inspection apparatus including a shape measurement unit, an image processor, a learning data set generator, a determination model generator, and a first determination unit.

The shape measurement unit measures the shape of the weld, and the image processor generates image data of the weld based on shape data measured. The learning data set generator classifies multiple pieces of image data by material and shape of a workpiece and performs data augmentation to generate a plurality of learning data sets. The determination model generator generates a determination model for the shape of the weld for each material and shape of the workpiece using the plurality of learning data sets. The first determination unit determines whether the shape of the weld is good or bad based on the image data read from the image processor and the determination model.

In an actual production processing site of workpieces, inspection conditions of the appearance inspection apparatus are changed as appropriate. For example, conditions such as an inspection speed for inspecting the weld along a welding line and a measurement frequency and measurement resolution of a sensor are successively changed to be optimum to the purpose of the user of the processing facility.

The inspection conditions are changed in this way because production takt time for the workpiece and inspection accuracy greatly vary depending on the inspection conditions. For example, when the production takt time is important, the inspection speed is set higher to perform the inspection in a shorter production takt time. However, this lowers the measurement resolution of the sensor, making the three-dimensional shape of the weld acquired by the sensor coarse. Thus, small weld defects cannot be detected, lowering the inspection accuracy.

When the inspection accuracy is important, the inspection speed is lowered to increase the measurement resolution. However, the lowered inspection speed increases the production takt time.

The inspection conditions are also changed depending on the status of the workpiece to be inspected or the weld. For example, the inspection speed may be changed depending on whether the shape of the workpiece is curved or linear. A product that does not allow any small defects requires more accurate inspection. In this case, the measurement resolution is increased at the cost of the production takt time.

Due to wide varieties of materials of the workpiece to be inspected and shapes of the welds, the inspection conditions are adjusted to the shapes of the welds.

However, for example, when the measurement resolution of the sensor changes, the measurement result differs even if the three-dimensional shape of the same weld is measured. Thus, the feature of the shape data of the weld inputted to the determination model does not match the feature of the shape data obtained in advance by machine learning, deteriorating the accuracy of the appearance inspection.

Further, machine learning for detecting the features of the shape requires a huge amount of shape data in the thousands to tens of thousands for each resolution. Acquiring the shape data for the machine learning for each of the different types of resolutions is practically difficult.

SUMMARY

In view of the foregoing, an object of the present disclosure is to provide an appearance inspection apparatus, a welding system, and a method for appearance inspection of a weld that allow accurate evaluation of the three-dimensional shape of the weld although inspection conditions are changed.

To achieve the object, the present disclosure is directed to an appearance inspection apparatus for inspecting an appearance of a weld of a workpiece. The appearance inspection apparatus includes at least: a shape measurement unit that is attached to a robot and configured to measure a three-dimensional shape of the weld along a welding line; and a data processor configured to process shape data acquired by the shape measurement unit. The data processor includes at least a shape data processor configured to perform at least removal of noise from sample shape data acquired in advance by the shape measurement unit, a first learning data set generator configured to generate a plurality of first learning data sets based on the sample shape data, a second learning data set generator configured to generate a plurality of second learning data sets based on each of the plurality of first learning data sets, a determination model generator configured to generate multiple types of determination models for determining whether the shape of the weld is good or bad using the plurality of second learning data sets, and a first determination unit configured to determine whether the shape of the weld is good or bad based on the shape data processed by the shape data processor and the determination models generated by the determination model generator.

A welding system of the present disclosure includes a welding apparatus configured to weld the workpiece and the appearance inspection apparatus. The welding apparatus includes at least a welding head configured to supply heat to the workpiece and an output controller configured to control a welding output of the welding head.

A method for appearance inspection of a weld of the present disclosure is a method for appearance inspection of a weld using the appearance inspection apparatus. The method includes at least: measuring the three-dimensional shape of the weld by the shape measurement unit moving together with the robot to acquire the sample shape data; generating the plurality of first learning data sets by the first learning data set generator based on the sample shape data; generating the plurality of second learning data sets by the second learning data set generator based on the plurality of first learning data sets; generating the multiple types of determination models for determining whether the shape of the weld is good or bad by the determination model generator using the plurality of second learning data sets;

measuring the three-dimensional shape of the weld by the shape measurement unit moving together with the robot to acquire the shape data; and determining whether the shape of the weld is good or bad by the first determination unit based on the shape data processed by the shape data processor and the determination models generated by the determination model generator. The determination models used by the first determination unit are generated based on at least one of the second learning data sets having a data density closest to a data density of the shape data processed by the shape data processor or at least one of the second learning data sets having a resolution closest to a resolution of the shape data corrected by the shape data processor.

According to the present disclosure, a three-dimensional shape of a weld can be accurately evaluated although inspection conditions are changed.

BRIEF DESCRIPTION OF THE DRAWINGS

FIG. 5B is a schematic view of a hardware configuration of a data processor.

FIG. 8A is a schematic view of a first example of a procedure for generating a second learning data set.

FIG. 8B is a schematic view of a second example of the procedure for generating the second learning data set.

FIG. 8D is a schematic view of a fourth example of the procedure for generating the second learning data set.

DETAILED DESCRIPTION

Embodiments of the present disclosure will be described below with reference to the drawings. The following description of the embodiments is merely an example in nature, and is not intended to limit the scope, applications, or use of the present invention.

EMBODIMENTS

[Configuration of Welding System]

Figure 1:
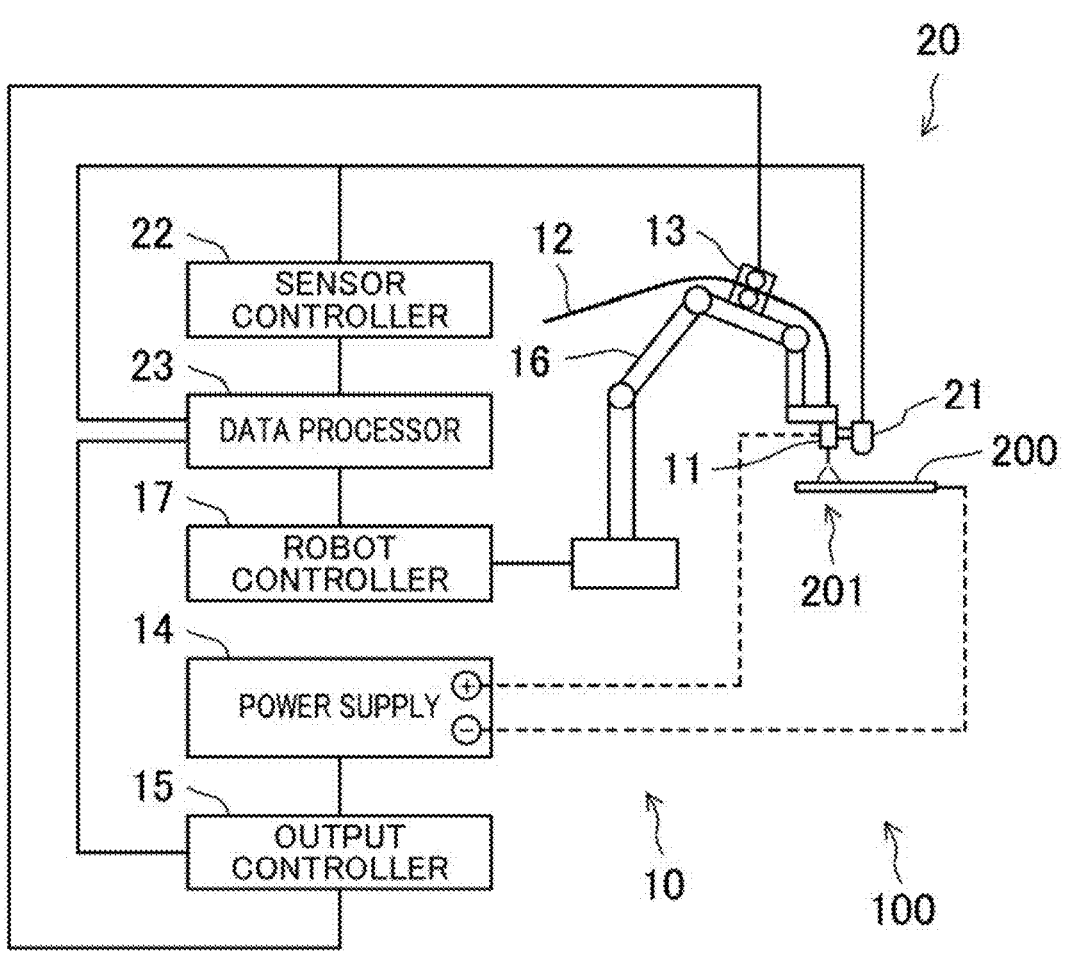
FIG. 1 is a schematic view of a configuration of a welding system according to an embodiment.

FIG. 1 is a schematic view of a configuration of a welding system of the present embodiment. A welding system 100 includes a welding apparatus 10 and an appearance inspection apparatus 20.

The welding apparatus 10 includes a welding torch 11, a wire feeder 13, a power supply 14, an output controller 15, a robot 16, and a robot controller 17. Electric power supplied from the power supply 14 to a welding wire 12 held by the welding torch 11 generates arc between the tip of the welding wire 12 and a workpiece 200, and heat is applied to the workpiece 200 to perform arc welding. Although the welding apparatus 10 includes other components and facilities such as a pipe and a gas cylinder for supplying shielding gas to the welding torch 11, such components are not illustrated and described for convenience of explanation. The power supply 14 may also be referred to as a welding power supply.

The output controller 15 is connected to the power supply 14 and the wire feeder 13 and controls a welding output of the welding torch 11, i.e., the electric power supplied to the welding wire 12 and power supply time, according to predetermined welding conditions. The output controller 15 also controls the speed and amount of the welding wire 12 fed from the wire feeder 13 to the welding torch 11. The welding conditions may be directly inputted to the output controller 15 via an input unit (not shown), or may be selected from a welding program read from a recording medium.

The robot 16, which is a known articulated robot, holds the welding torch 11 at the tip, and is connected to the robot controller 17. The robot controller 17 controls the motion of the robot 16 so that the tip of the welding torch 11, in other words, the tip of the welding wire 12 held by the welding torch 11, moves to a desired position along a predetermined welding path.

Figure 2:
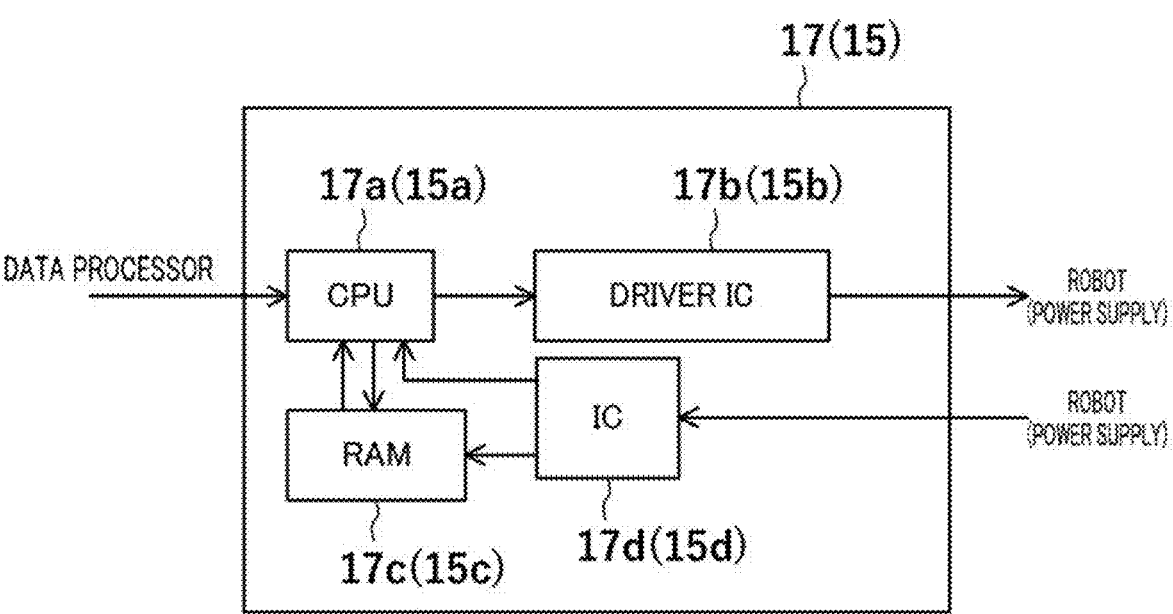
FIG. 2 is a schematic view of a hardware configuration of a robot processor.

FIG. 2 is a schematic view of a hardware configuration of a robot processor. The robot controller 17 includes at least a central processing unit (CPU) 17a, a driver integrated circuit (IC) 17b, random access memory (RAM) 17c, and an integrated circuit (IC) 17d.

In normal operation, the IC 17d receives signals outputted from rotation detectors (not shown) provided on a plurality of articulated shafts of the robot 16. The outputted signals are processed by the IC 17d and inputted to the CPU 17a. The CPU 17a transmits a control signal to the driver IC 17b based on the signals inputted from the IC 17d and the rotation rate of the articulated shafts set in a predetermined program stored in the RAM 17c. The driver IC 17b controls the rotation of servo motors (not shown) connected to the articulated shafts based on the control signals from the CPU 17a.

As will be described later, when the shape of a weld 201 is determined to be bad by a first determination unit 28 of a data processor 23 of the appearance inspection apparatus 20, the CPU 17a of the robot controller 17 that received the determination result stops the motion of the robot 16 or moves the robot 16 so that the welding torch 11 moves to a predetermined initial position.

The output controller 15 also has the same configuration as the robot controller 17. That is, the output controller 15 includes at least a CPU 15a, a driver IC 15b, RAM 15c, and an IC 15d.

In normal operation, the IC 15d receives a signal corresponding to the output of the power supply 14. The signal is processed by the IC 15d and inputted to the CPU 15a. The CPU 15a transmits a control signal to the driver IC 15b based on the signals inputted from the IC 15d and the output of the power supply 14 set in a predetermined program stored in the RAM 15c. The driver IC 15b controls the output of the power supply 14 and the welding output of the welding torch 11 based on the control signal from the CPU 15a.

As will be described later, when the shape of the weld 201 is determined to be bad by the first determination unit 28 of the appearance inspection apparatus 20, the CPU 15a of the output controller 15 that received the determination result stops the output of the power supply 14. Thus, the welding output of the welding torch 11 is stopped.

Both of the output controller 15 and the robot controller 17 may include other components than those shown in FIG. 2. For example, read only memory (ROM) or a hard disk drive (HDD) may be included as a storage device.

The appearance inspection apparatus 20 includes a shape measurement unit 21, a sensor controller 22, and a data processor 23. The shape measurement unit 21 is attached to the robot 16 or the welding torch 11 to measure the shape of the weld 201 of the workpiece 200. The configuration of the appearance inspection apparatus 20 will be described in detail later.

FIG. 1 shows an arc welding apparatus configured to perform arc welding as the welding apparatus 10, but the welding apparatus 10 is not particularly limited to the arc welding apparatus. For example, the welding apparatus 10 may be a laser welding apparatus configured to perform laser welding. In this case, a laser head (not shown) connected to a laser oscillator (not shown) via an optical fiber (not shown) is attached to and held by the robot 16 in place of the welding torch 11. In the following description, the welding torch 11 and the laser head may be collectively referred to as a welding head 11.

[Configuration of Appearance Inspection Apparatus]

Figure 3:
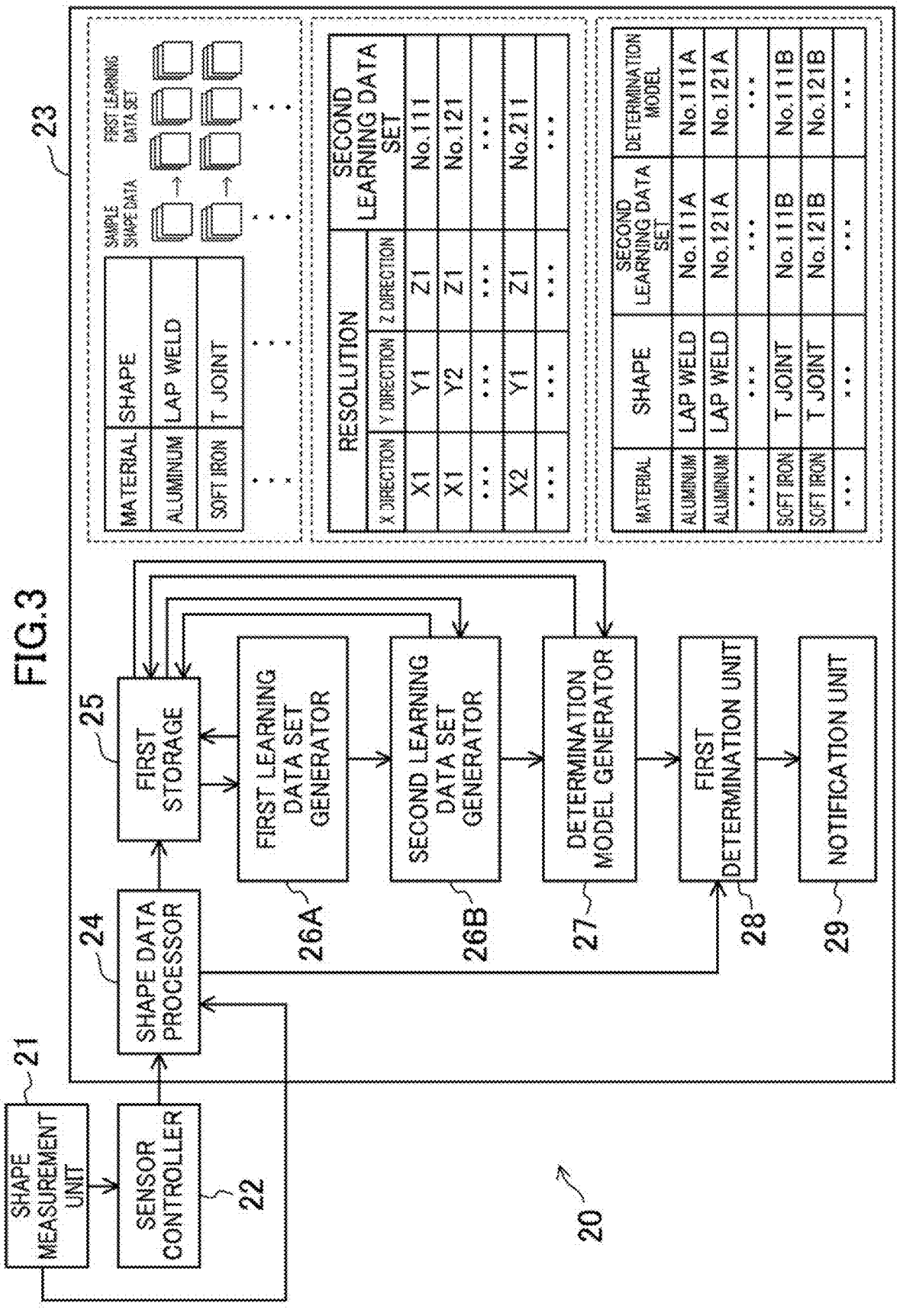
FIG. 3 is a functional block diagram of an appearance inspection apparatus.
Figure 4:
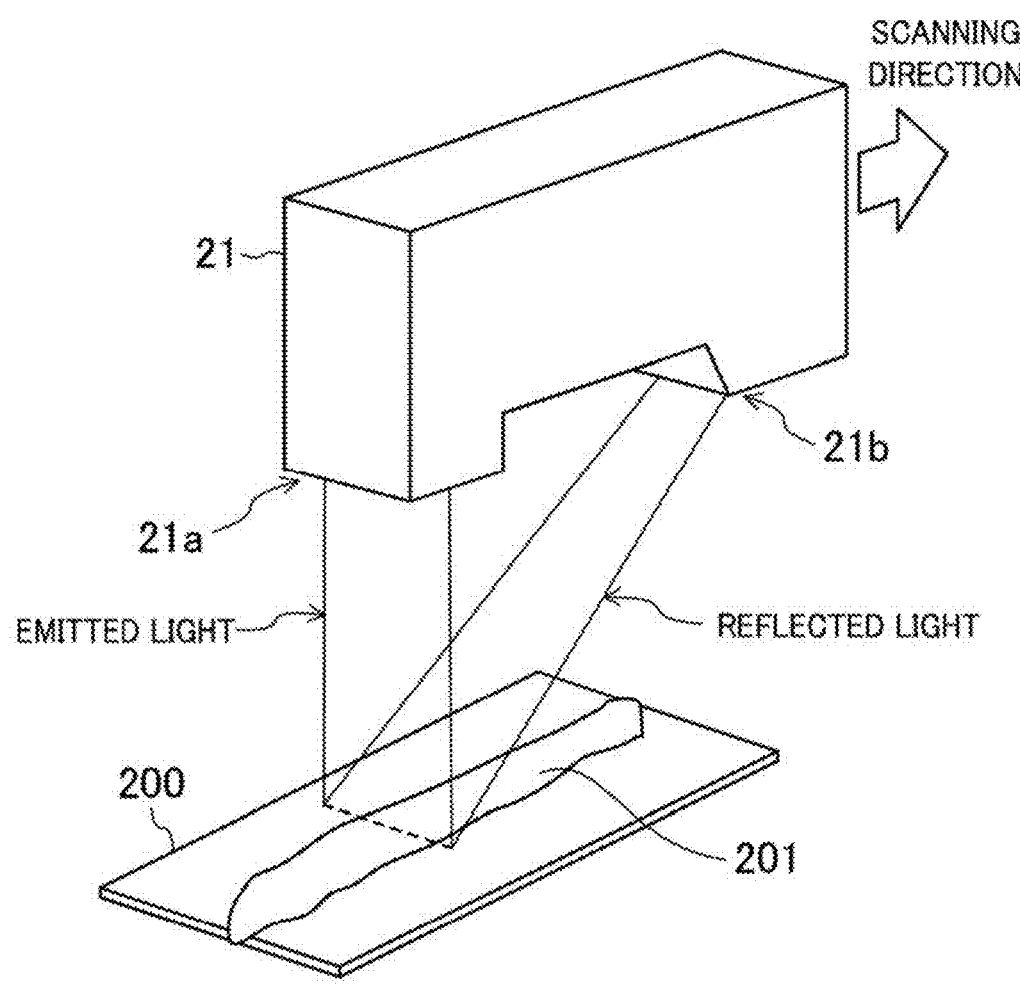
FIG. 4 is a schematic view of measurement of the shape of a weld bead by a shape measurement unit.
Figure 4:
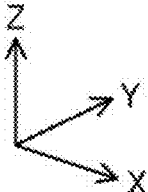
Figure 5A:
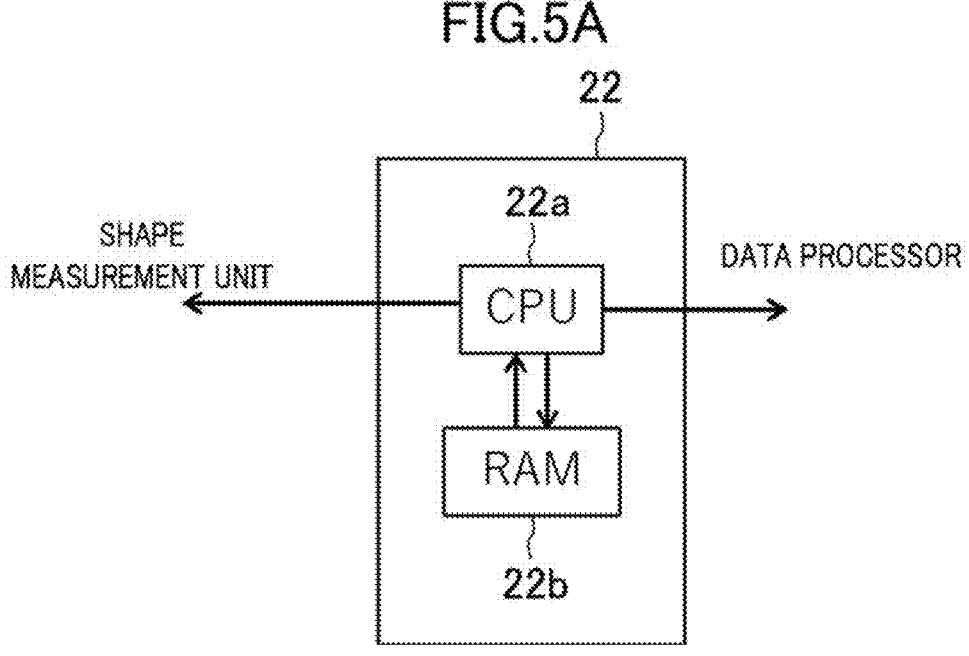
FIG. 5A is a schematic view of a hardware configuration of a sensor controller.
Figure 5B:
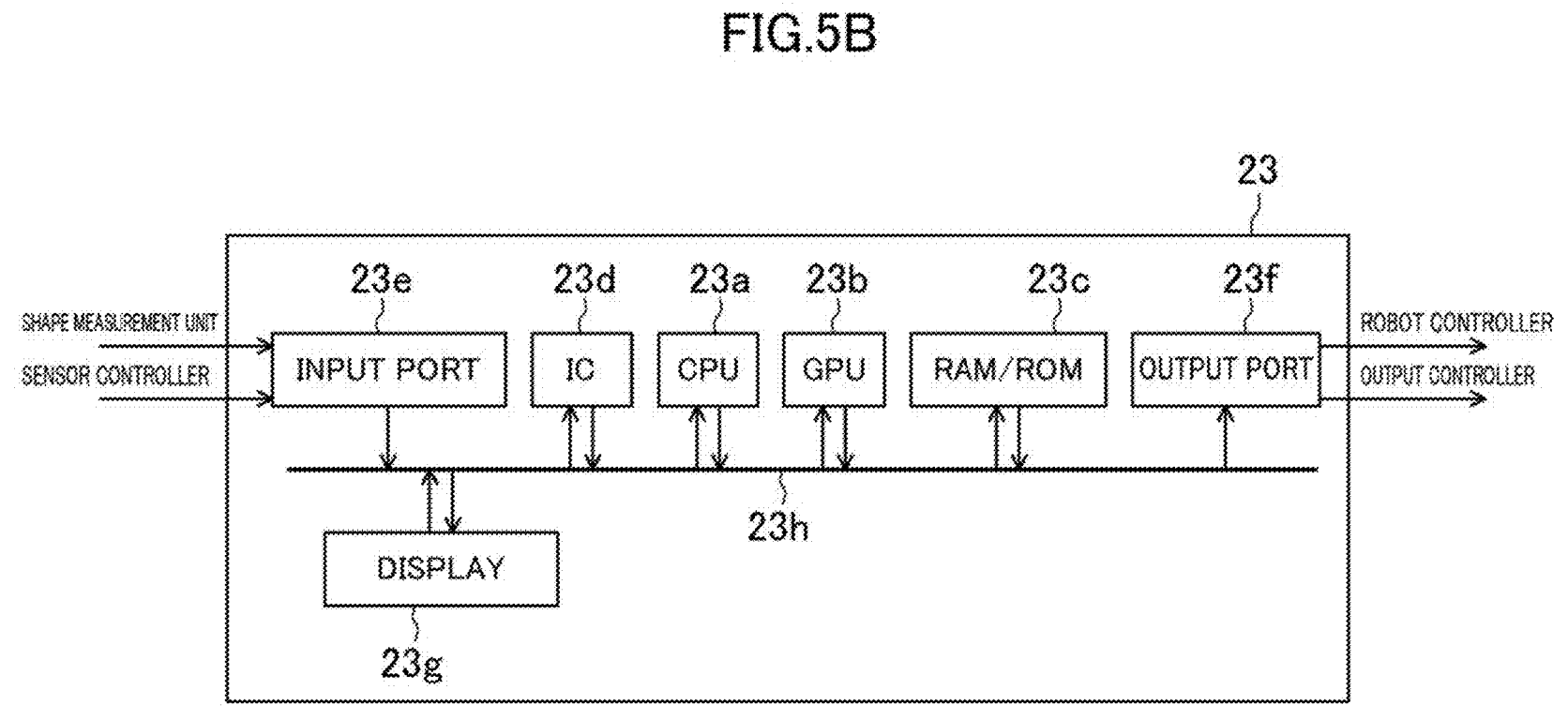

FIG. 3 is a functional block diagram of the appearance inspection apparatus, and FIG. 4 is a schematic view of measurement of the shape of a weld bead by the shape measurement unit. FIG. 5A is a schematic view of a hardware configuration of the sensor controller, and FIG. 5B is a schematic view of a hardware configuration of the data processor.

The shape measurement unit 21 is, for example, a three-dimensional shape measurement sensor including a laser beam source 21a capable of scanning the surface of the workpiece 200 (see FIG. 4) and a camera (not shown) configured to capture an image of a reflection trajectory (will be hereinafter referred to as a shape line) of a laser beam projected onto the surface of the workpiece 200 or a light receiving sensor array 21b (see FIG. 4).

As shown in FIG. 4, the shape measurement unit 21 scans a predetermined region including the weld 201 and its periphery with the laser beam (emitted light) and captures an image of the emitted light reflected by the surface of the workpiece 200 by the light receiving sensor array 21b to measure the three-dimensional shape of the weld 201. The weld 201 is a so-called weld bead formed in a direction along a welding line set in advance by a welding program. In the following description, the direction along the welding line may be referred to as a Y direction (see FIG. 6A). A direction orthogonal to the Y direction on the surface of the workpiece 200 on which the weld 201 is formed may be referred to as an X direction. A direction of the height of the weld 201 with respect to the surface of the workpiece 200 may be referred to as a Z direction. The Z direction is orthogonal to the X direction and the Y direction.

In the present specification, objects being "orthogonal," "parallel," or "the same" are orthogonal, parallel, or the same to the degree that allows manufacturing tolerances and assembly tolerances of the components constituting the welding system 100, machining tolerances of the workpiece 200, and variations in the travel speed of the robot 16. This does not mean that the objects are orthogonal, parallel, or the same in a strict sense.

In the example shown in FIG. 4, the light emitted from the laser beam source 21a is applied to multiple points in the width direction of the weld 201, in this case, the X direction. The laser beam is reflected from the multiple points and captured by the light receiving sensor array 21b. The shape measurement unit 21 held by the robot 16 travels at a predetermined speed in the Y direction. During the travel, the light is emitted at predetermined time intervals to irradiate the weld 201 and its periphery, and the light receiving sensor array 21b captures an image of the reflection of the light each time the light is emitted.

As described above, the shape measurement unit 21 is configured to measure the shape of, not only the weld 201, but also its periphery, in a predetermined range. This is for determining whether spatters 204 and smuts 206 described later (see FIG. 6A) are present or not.

The term "measurement resolution" refers to a distance between measurement points adjacent to each other in shape data measured by the shape measurement unit 21. For example, the measurement resolution in the X direction is a distance between measurement points adjacent to each other in the X direction. The measurement resolution in the X direction is set according to the capability of the shape measurement unit 21, mainly of the light receiving sensor array 21b, and more specifically, the size in the X direction of each sensor included in the light receiving sensor array 21b and the distance between the sensors.

The measurement resolution is set in each of the X, Y, and Z directions. As will be described later, the measurement resolution in the Y direction varies depending on the travel speed of the robot 16 or the sampling frequency of the light receiving sensor array 21b.

When simply referred to as a "resolution," it means an interval between coordinate points adjacent to each other in multiple pieces of point group data of the weld 201 acquired by the shape measurement unit 21. As will be described later, the shape data is reconstructed in accordance with the shape of the weld 201. The resolution of the shape data before the reconstruction is the same as the measurement resolution described above. The resolution of the reconstructed shape data may be different from the measurement resolution. In the example shown in this specification, the X-direction resolution of the shape data is the same as the measurement resolution in the X direction. However, the Y-direction resolution of the shape data may be different from the measurement resolution in the Y direction. The resolution is set in each of the X, Y, and Z directions.

As shown in FIG. 5A, the sensor controller 22 includes at least a CPU 22*a* and RAM 22*b*. In the sensor controller 22, the CPU 22*a* transmits a control command to the shape measurement unit 21 to control the operation of the shape measurement unit 21. The control command transmitted from the CPU 22*a* to the shape measurement unit 21 includes, for example, conditions for inspection by the shape measurement unit 21 and a command to start or stop the measurement by the shape measurement unit 21. The RAM 22*b* stores preset inspection conditions. The RAM 22*b* may store other types of data. The sensor controller 22 may include other components than those shown in FIG. 5A. For example, ROM or an HDD may be included as the storage device.

The data processor 23 receives the point group data of the shape line acquired by the shape measurement unit 21 as the shape data and processes the shape data.

As shown in FIG. 3, the data processor 23 includes a plurality of functional blocks. Specifically, the data processor 23 includes a shape data processor 24, a first storage 25, a first learning data set generator 26A, a second learning data set generator 26B, a determination model generator 27, a first determination unit 28, and a notification unit 29.

As shown in FIG. 5B, the data processor 23 includes, as hardware, at least a CPU 23*a*, a graphics processing unit (GPU) 23*b*, RAM/ROM 23*c*, an IC 23*d*, an input port 23*e*, an output port 23*f*, and a data bus 23*h*. The data processor 23 includes a display 23*g*.

The data processor 23 shown in FIG. 5B has the same hardware configuration as a known personal computer (PC). The functional blocks in the data processor 23 shown in FIG. 3 are implemented by running predetermined software in various devices shown in FIG. 5B, particularly the CPU 23*a* and the GPU 23*b*. Although FIG. 5B shows an example in which various devices are connected to the single data bus 23*h*, two or more data buses may be provided depending on the purpose, as in the case of an ordinary PC.

The shape data processor 24 of the data processor 23 has the function of removing noise from the shape data acquired by the shape measurement unit 21. The reflectance of the laser beam emitted from the shape measurement unit 21 varies depending on the material of the workpiece 200. An excessive reflectance causes halation as noise, affecting the shape data. Thus, the shape data processor 24 is configured to perform a noise filtering process on the software. The noise can also be removed by an optical filter (not shown) provided for the shape measurement unit 21 itself. Combined use of the optical filter and the filtering process on the software can provide high quality shape data. This can improve the quality of a determination model of a learning data set described later, and whether the shape of the weld 201 is good or bad can be determined with accuracy.

The noise removal function of the shape data processor 24 is mainly implemented by the IC 23*d* of the data processor 23. However, the present invention is not limited to this example, and the noise may be removed from the shape data by the GPU 23*b* of the data processor 23, for example.

The shape data processor 24 corrects an inclination and distortion of a base portion of the weld 201 with respect to a predetermined reference plane, for example, an installation surface of the workpiece 200, by statistically processing the point group data. The shape data processor 24 may also perform, for example, edge enhancement correction, by enhancing the periphery of the weld 201 to emphasize the shape and location of the weld 201.

The shape data processor 24 extracts feature values of the shape data in accordance with the shape of the workpiece 200 or inspection items for the shape of the weld 201. In this case, one or more feature values corresponding to one or more inspection items are extracted for a piece of shape data. The extracted feature values are associated with the shape data for use in subsequent data processing. The feature values are particular specifications extracted from the shape data. Typical examples thereof include a length, width, and height from the reference plane of the weld 201, and a difference in length, width, and height between a plurality of points in the weld 201. However, the feature values are not particularly limited to such specifications, and are appropriately set according to the details to be evaluated in terms of the inspection items.

The shape data processor 24 is configured to be able to convert/correct the resolution of the acquired shape data. The conversion/correction of the resolution of the shape data will be described in detail later.

The CPU 23*a* of the data processor 23 mainly implements the functions of edge enhancement correction, feature value extraction, and conversion/correction of the resolution of the shape data processor 24. However, the present invention is not particularly limited to this example, and the IC 23*d* or the GPU 23*b* may perform part or all of the edge enhancement correction.

The first storage 25 stores shape data of the weld 201 of a different workpiece 200 processed before the welding of the workpiece 200 as an evaluation target. The first storage 25 stores the shape data experimentally acquired in advance before welding the actual workpiece 200. In the following description, the shape data acquired in advance may be referred to as sample shape data.

The sample shape data includes non-defective data about a good shape of the weld 201 to be evaluated and defective data about a shape with some defects. The defective data is processed into multiple pieces of learning data by changing the number and locations of shape defects and labelling the shape defects with types of the shape defects. The defective data after the labelling and the non-defective data are collectively used as a learning data set before data augmentation. Needless to say, the shape data of the weld 201 of the other workpiece 200 and the shape data of the weld 201 of the target workpiece 200 are acquired from similar welds 201 of the workpieces 200 having the similar shape and being made of the same material.

For the acquisition of the sample shape data, the conditions for the inspection by the shape measurement unit 21 are fixed. However, the inspection conditions may be changed for each material or shape of the workpiece 200. The first storage 25 also stores first learning data sets, second learning data sets, and determination models that will be described later.

The first learning data set generator 26A reads the sample shape data generated by the shape data processor 24 and stored in the first storage 25 and classifies the data by material and shape of the workpiece 200. The sample shape data may be classified by inspection item of the weld 201. In this case, the same learning data may be included in different inspection items. The first learning data set generator 26A generates a first learning data set based on the classified sample shape data. Specifically, the first learning data set generator 26A generates the first learning data set based on the feature values associated with the sample shape data. The first learning data set is generated for each material and shape of the workpiece 200. For example, the materials and shapes of the workpiece 200 are sorted into a matrix to determine classification categories, and the first learning data sets are classified in correspondence with the categories. Examples of the shapes of the workpiece 200 include a butt weld and lap weld of plates, a T joint, and a cross joint.

The first learning data set generator 26A performs data augmentation on the sample shape data to generate the first learning data set. Specifically, one or more feature values associated with the sample shape data are changed, or the position of the shape defect in the sample shape data is changed. Alternatively, both processes are performed for the data augmentation. That is, multiple types of first learning data sets are generated from a piece of sample shape data.

The second learning data set generator 26B reads the first learning data set generated by the first learning data set generator 26A and stored in the first storage 25 to generate the second learning data set. The second learning data set is a group of learning data that is inputted to a determination model described later and is used to improve the determination accuracy of the determination model.

The second learning data set is generated by changing the data density of the first learning data set in several different ratios. Alternatively, the second learning data set is generated by changing the resolution of the first learning data set in several different ratios. Specifically, the second learning data set generator 26B generates a plurality of second learning data sets corresponding to the types and the number of the first learning data sets stored in the first storage 25. The term "data density" refers to the density of multiple pieces of point group data in the weld 201, the first learning data sets, and the second learning data sets acquired by the shape measurement unit 21. In the present specification, the density mainly refers to the density of the point group data in an XY plane including the X direction and the Y direction. In the example shown in FIG. 3, the second learning data sets are generated by changing the resolutions in the X direction, Y direction, and Z direction of the first learning data sets, and each of the generated data sets is numbered and stored in the first storage 25. A procedure for generating the first and second learning data sets will be described in detail later.

The functions of the first learning data set generator 26A and the second learning data set generator 26B are mainly implemented by the CPU 23a of the data processor 23. However, the present invention is not particularly limited to this example, and the GPU 23b may implement part of the functions.

The determination model generator 27 generates a determination model based on a determination criterion set for each of the inspection items of the weld 201 set for each material and shape of the workpiece 200. The generated determination model is represented as, for example, a combination of two or more discriminators each of which is weighed. The determination model is, for example, a known object detection algorithm expressed by a convolutional neural network (CNN).

The determination model generator 27 inputs, to each of the determination models generated for each material and shape of the workpiece 200, the second learning data set for each material and shape of the workpiece 200, among the second learning data sets having the same data density or the same resolution. The learning is repeated to improve the determination accuracy of each determination model. In this case, the determination models are generated according to the classification categories shown in FIG. 3. The learning is repeated until the accuracy rate, recall rate, and precision of the determination model satisfy preset values. In the example shown in FIG. 3, multiple second learning data sets having the resolutions varied for each material and shape of the workpiece 200 are prepared. The determination models are generated to correspond to the second learning data sets, and each of the determination models is numbered and stored in the first storage 25.

The determination model can be generated in a shorter time with higher accuracy when the non-defective data and the defective data in the sample shape data are suitably selected and used according to the material and shape of the workpiece 200. Likewise, the determination model can be generated in a shorter time with higher accuracy for each inspection item of the weld 201 when the non-defective data and the defective data in the sample shape data are suitably selected and used according to the inspection items.

The first determination unit 28 determines whether the shape of the weld 201 is good or bad, i.e., whether the shape satisfies a predetermined criterion, based on the shape data of the weld 201 on which the processes such as noise removal and edge enhancement have been done by the shape data processor 24 and the determination model corresponding to the selected inspection item among the determination models generated by the determination model generator 27. The second learning data set used to generate the determination model has the same data density or the same resolution as the shape data of the weld 201 acquired by the shape data processor 24. In other words, the first learning data set used to generate the second learning data set is selected to have the same data density as the shape data of the weld 201 acquired by the shape data processor 24. Alternatively, the first learning data set used to generate the second learning data set is selected to have the same resolution as the shape data of the weld 201 acquired by the shape data processor 24.

Before the determination of whether the shape of the weld 201 is good or bad, the determination model is reinforced by learning using the second learning data set. Specifically, as for the selected inspection item, the second learning data set generated by the second learning data set generator 26B is inputted to the determination model generated by the determination model generator 27.

The determination result is manually checked by an operator such as a welder. When the type of the weld defect does not match the learning data, annotation is executed. The annotation refers to a process of tagging the presence of the shape defect identified by visually checking the actual weld 201 together with the type of the shape defect to a corresponding part of the shape data. This annotation is basically manually performed.

By performing the annotation, whether the shape defect is present and the type of the shape defect are revised in the learning data. Based on the result of the annotation, the second learning data set is regenerated or a new second learning data set is generated, and the relearning of the determination model is performed using the annotated second learning data set. By repeating these processes one or more times, the determination model is reinforced by learning.

However, as will be described later, the shape defect has a variety of modes. In practice, which mode the shape defect included in the shape data has is calculated in terms of probability. If the probability is equal to or higher than a predetermined value, the shape defect is determined to be present, and the type of the shape defect is identified. This will be described in detail later.

For example, the degree of coincidence between the type of the shape defect annotated in the learning data and the type of the shape defect included in the shape data of the weld 201 is determined by probability. When the probability exceeds a predetermined threshold, the type of the shape defect included in the shape data of the weld 201 is identified.

The first determination unit 28 outputs the following information. Specifically, the first determination unit 28 outputs whether the shape defect is present or not, and outputs, if the shape defect is present, the type, number, size, and location of the shape defect in the weld 201. When the number of the shape defects exceeds a threshold according to a predetermined determination criterion, the first determination unit 28 outputs the result of the determination of whether the shape of the weld 201 is good or bad. The threshold varies depending on the type and size of the shape defect. For example, if five or more spatters described later (see FIG. 6A) having a diameter of 5 μm or more are present, the shape of the weld 201 is determined to be bad. If one or more holes (see FIGS. 6A and 6C) are present, the shape of the weld 201 is determined to be bad. These are merely examples and can be changed as appropriate in accordance with the above-described determination criterion and the threshold.

The threshold for determining the shape defect and a format for displaying the shape defect can be optionally set. For example, the shape defect may be displayed in red if identified as the spatter 204, or in yellow if identified as a hole 202 (see FIG. 6A). If the presence or absence of the spatters 204 and the upper limit number of the spatters 204 are set as the inspection items, a portion recognized as the spatter 204 may be displayed in a color different from its background, and the probability that the portion is the spatter 204 may be classified by color. Thus, the welder or a system administrator can easily recognize the presence or absence of the shape defects and the degree of distribution of the shape defects at a glance. For example, the probability of the degree of coincidence may be colored in green if the probability is 30% or less, or in red if the probability is 70% or more. Needless to say, this classification of the probability ranges by color and the definition of the colors can be arbitrarily set. If the criterion for determining whether the shape is good or bad includes the size of the spatters 204, it is needless to say that the size of the spatters 204 calculated based on the shape data is compared with the criterion to determine whether the shape is good or bad. The shape of the weld 201 is inspected for a variety of inspection items, and whether the shape is good or bad is determined for each inspection item. The product is finally determined to be good only when the shape of the weld 201 has satisfied all the inspection items for which the determination is necessary.

The notification unit 29 is configured to notify the output controller 15, the robot controller 17, the welder, or the system administrator of the result of the determination by the first determination unit 28. For example, the display 23g of the data processor 23 corresponds to the notification unit 29. For the notification, the determination result may be shown on the display 23g or a display unit (not shown) of the welding system 100 and/or may be outputted from a printer (not shown). If only a simple notification of the final determination result is sufficient, voice notifying the result may be outputted from an audio output unit which is not shown. In a preferred embodiment, the notification unit 29 notifies not only the final determination result, but also the determination result for each inspection item. The notification in this manner allows the welder or the system administrator to specifically realize what kind of defect the weld 201 has.

If the result of the determination by the first determination unit 28 is positive, i.e., the shape of the weld 201 is determined to be good, the welding system 100 continuously welds a portion 201 to be welded next of the same workpiece 200, or a similar portion 201 to be welded of a next workpiece 200.

If the result of the determination by the first determination unit 28 is negative, i.e., the shape of the weld 201 is determined to be bad, the output controller 15 stops the welding output of the welding torch 11, and the robot controller 17 stops the motion of the robot 16 or operates the robot arm 16 so that the welding torch 11 moves to a predetermined initial position.

[Procedure for Generating Determination Model]

FIGS. 6A to 6E show examples of the shape defect generated in the weld. FIGS. 7A to 7C are schematic views of first to third examples of a procedure for generating the first learning data set. FIGS. 8A to 8D are schematic views of first to fourth examples of a procedure for generating the second learning data set.

Figure 6A:
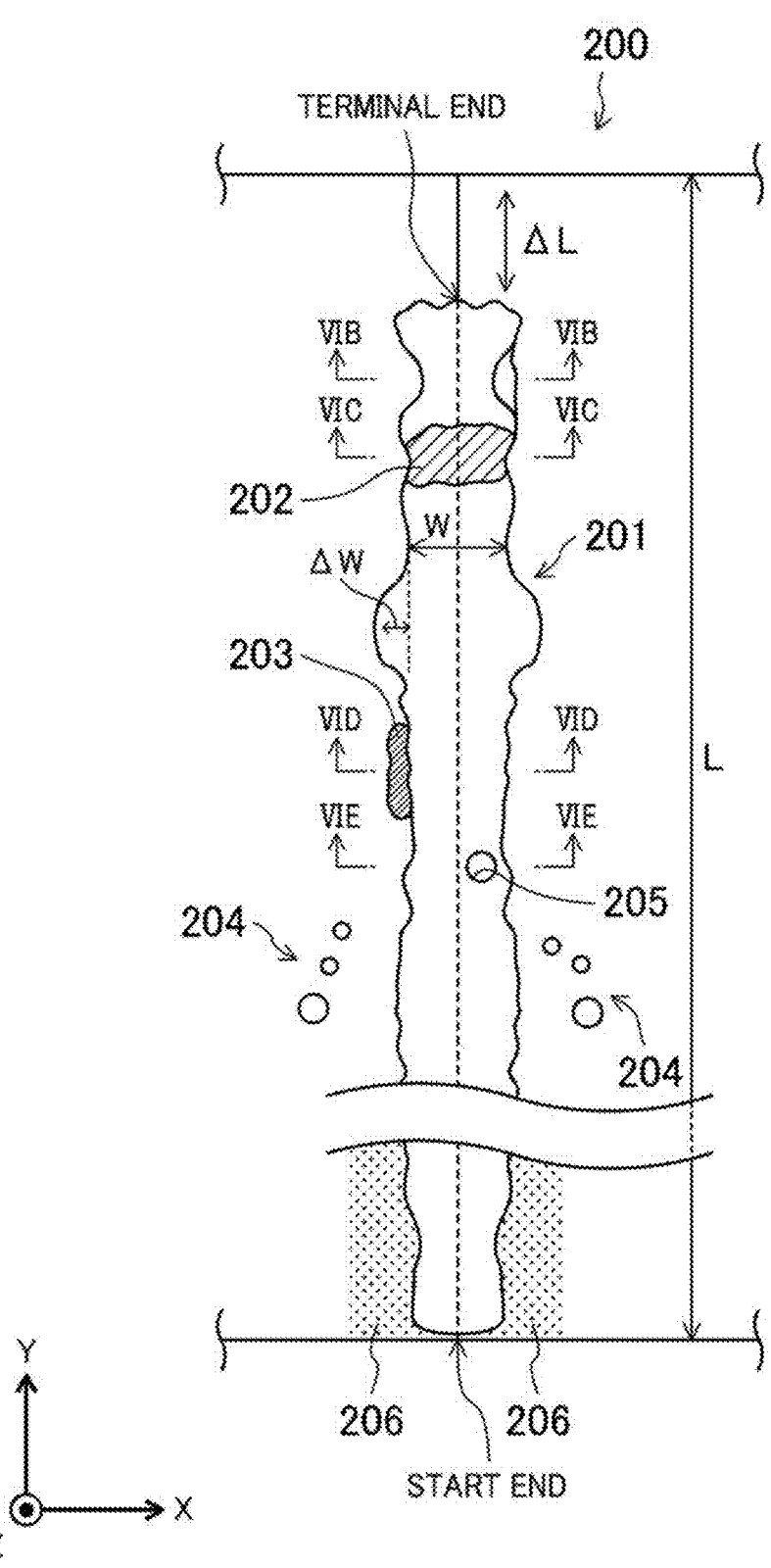
FIG. 6A is a schematic plan view of an example of a defective mode of a weld.

FIGS. 6A to 6E show the shape of the weld 201 which is butt-welded. FIG. 6A shows a planar shape, and FIGS. 6B to 6E show cross-sectional views taken along line VIB-VIB or line VIE-VIE of FIG. 6A. In FIGS. 8A to 8D, coordinate points are indicated by open circles only around the weld 201 and the spatter 204 for convenience of description.

Figure 9:
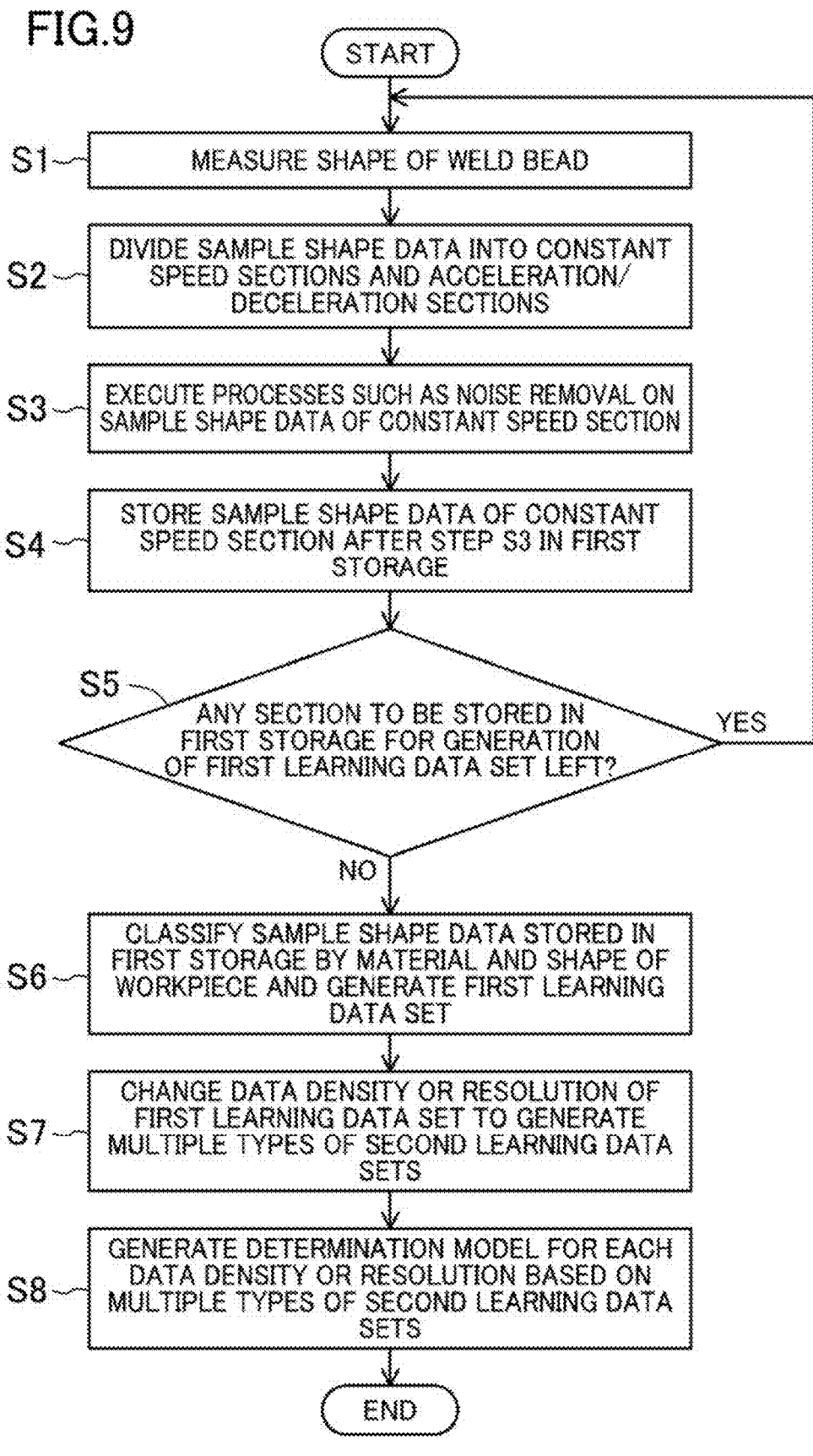
FIG. 9 is a flowchart of a procedure for generating determination models.

FIG. 9 is a flowchart of a procedure for generating the determination model. The procedure for generating the determination model will be described below with reference to the flowchart.

First, the shape of the weld 201 is measured by the shape measurement unit 21 (Step S1) to acquire sample shape data.

Next, the data processor 23 acquires the travel speed of the robot 16, that is, the speed of the shape measurement unit 21 scanning the weld 201 in the Y direction, from the robot controller 17. The data processor 23 divides a section scanned by the shape measurement unit 21 in the Y direction into constant speed sections of a predetermined length based on the travel speed of the robot 16. Alternatively, the data processor 23 divides the section scanned by the shape measurement unit 21 in the Y direction into a constant speed section and an acceleration/deceleration section (Step S2). The "constant speed section" refers to a section in which the shape measurement unit 21 attached to the robot 16 travels at a constant speed in the Y direction. The "acceleration/ deceleration section" refers to a section in which the shape measurement unit 21 attached to the robot 16 travels at an accelerating speed, a decelerating speed, or both accelerating and decelerating speeds, in the Y direction.

The shape data processor 24 performs the above-described processes such as edge enhancement correction and noise removal on the sample shape data in the constant speed section among the sections divided in Step S2 (Step S3). The sample shape data obtained after the process of Step S3 is stored in the first storage 25 (Step S4).

Next, the shape data processor 24 determines whether any of the welds 201 formed on the workpiece 200 remains unmeasured (Step S5). If the determination result of Step S5 is positive, the process returns to Step S1 to measure the shape of the unmeasured welds. If the determination result of Step S5 is negative, the process proceeds to Step S6. Measurement of all necessary portions and conversion of the measured shape into data collect a required amount of sample shape data used to generate the first learning data sets and the second learning data sets. The sample shape data obtained after the processes such as the measurement and the noise removal is stored in the first storage 25.

The first learning data set generator 26A reads the sample shape data stored in the first storage 25 and classifies the data by material and shape of the workpiece 200. The first learning data set generator 26A performs data augmentation on the sample shape data to generate the first learning data set (Step S6). The procedure for generating the first learning data set will be further described below.

As shown in FIGS. 6A to 6E, when the workpiece 200 is arc-welded or laser-welded, the weld 201 may have various kinds of shape defect depending on, for example, poor setting of the welding conditions and low quality of the workpiece 200 used. For example, the weld 201 may partially melt off (a through hole formed in the workpiece 200 when the weld 201 partially melts off the workpiece 200 may be hereinafter referred to as a hole 202), or an undercut 203 may be formed. The undercut 203 means a defective portion that is formed at an edge of a weld bead and is dented from the surface of the workpiece 200. The length, width, and height from the reference plane of the weld 201 may vary from their design values L, W, and H beyond allowable ranges ΔL, ΔW, and ΔH. Further, when droplets (not shown) generated at the tip of the welding wire 12 move to the workpiece 200, some of the droplets or fine particles of molten metal of the workpiece 200 may be scattered to generate the spatters 204. When the workpiece 200 is a galvanized steel sheet, the sheet may partially evaporate from the weld 201 to leave a pit 205. When the workpiece 200 or the welding wire 12 is made of an aluminum-based material, smut 206 may be generated near the weld 201.

The pit 205 opens at the surface of the weld bead, and the smut 206 is a black soot-like product that adheres to the vicinity of the weld bead. The pit 205 and the smut 206, and the above-described hole 202, undercut 203, and spatter 204 as well, are examples of the modes (types) of the shape defect.

As described above, the shape defect of the weld 201 has various modes, for each of which the determination criterion is required to perform the inspection in accordance with the criterion. For the hole 202 or the undercut 203, whether the shape is good or bad needs to be determined not only by its presence or absence, but also by setting, for example, a contrast ratio to or a height difference from the periphery of the weld 201, to identify the hole 202 or the undercut 203. For the spatters 204, for example, it is necessary to obtain its average diameter and determine whether the shape is good or bad by the number of the spatters 204 having an average diameter equal to or greater than a predetermined value per unit area. The number of inspection items and the criterion for determining whether the shape of the weld 201 is good or bad are changed or increased depending on the material and portion to be welded of the workpiece 200 and specifications required by the customer.

The criterion for determining whether the shape defect is present from the shape data varies depending on the material and shape of the workpiece 200. As described above, the reflectance of the laser beam varies depending on the material of the workpiece 200, and for example, the luminance level and contrast of the shape data also vary. For welding straight portions having the same length, the shape of the bead of the weld 201 may vary due to the influence of gravity depending on the shape of the workpiece 200.

Thus, the determination model generator 27 needs to generate the determination models using a large amount of learning data for each material and shape of the workpiece 200. That is, a large amount of shape data of the weld 201 suitable as the learning data needs to be acquired for each material and shape of the workpiece 200. However, acquiring the sample shape data necessary for each material and shape of the workpiece 200 in advance involves enormous number of man-hours, which is inefficient.

Thus, according to the present embodiment, the first learning data set generator 26A classifies the sample shape data read from the first storage 25 by material and shape of the workpiece 200 and performs data augmentation on each of the classified pieces of sample shape data to generate a plurality of first learning data sets.

For example, as shown in FIG. 6A, the length and position of the weld 201, which are feature values, in the original sample shape data are varied to generate multiple pieces of data as the first learning data set. In an example shown in FIG. 6A, the first learning data sets in each of which the length of the weld 201 is smaller than the reference value L beyond the allowable range ΔL are generated. However, the present invention is not particularly limited to this example, and the first learning data sets in each of which the length is greater than the reference value L beyond the allowable range ΔL are also generated.

Figure 6B:
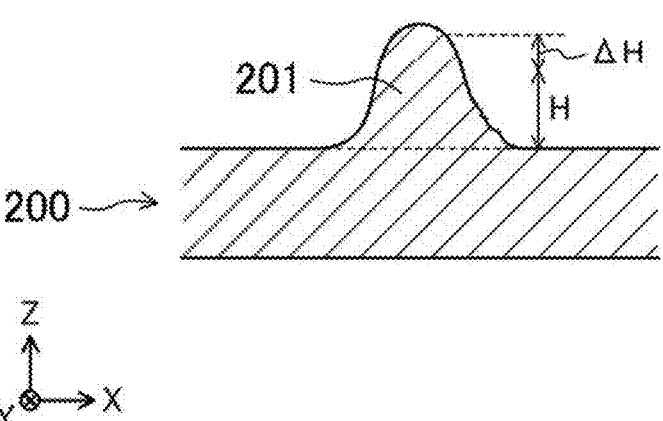
FIG. 6B is a schematic cross-sectional view taken along line VIB-VIB of FIG. 6A.
Figure 6C:
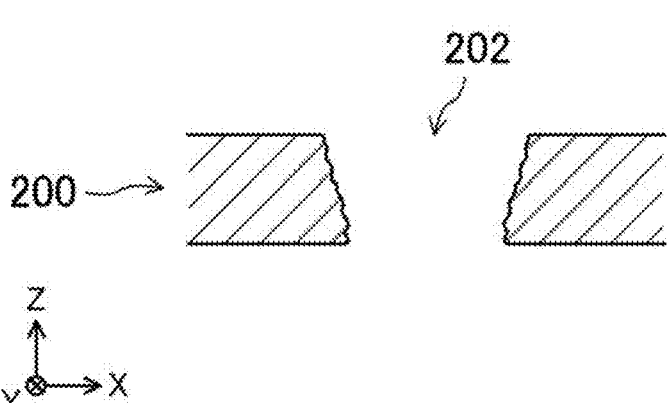
FIG. 6C is a schematic cross-sectional view taken along line VIC-VIC of FIG. 6A.
Figure 6D:
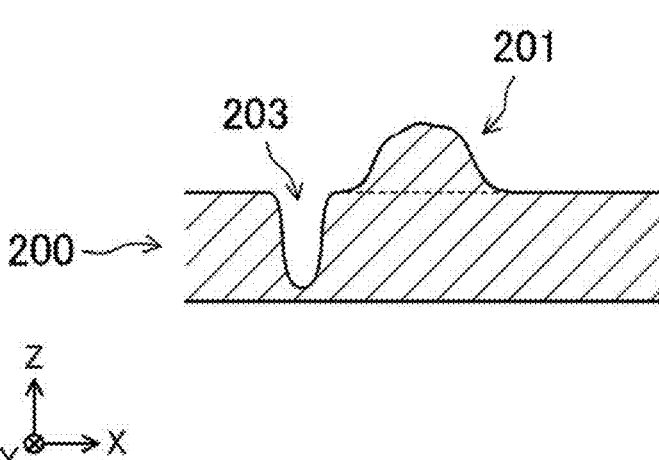
FIG. 6D is a schematic cross-sectional view taken along line VID-VID of FIG. 6A.
Figure 6E:
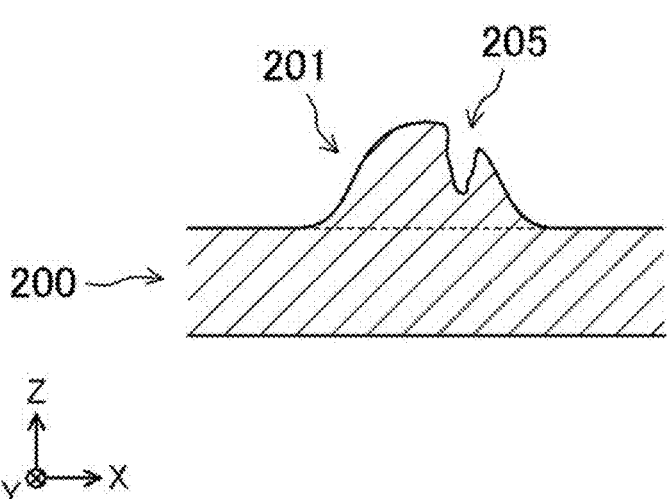
FIG. 6E is a schematic cross-sectional view taken along line VIE-VIE of FIG. 6A.
Figure 7A:
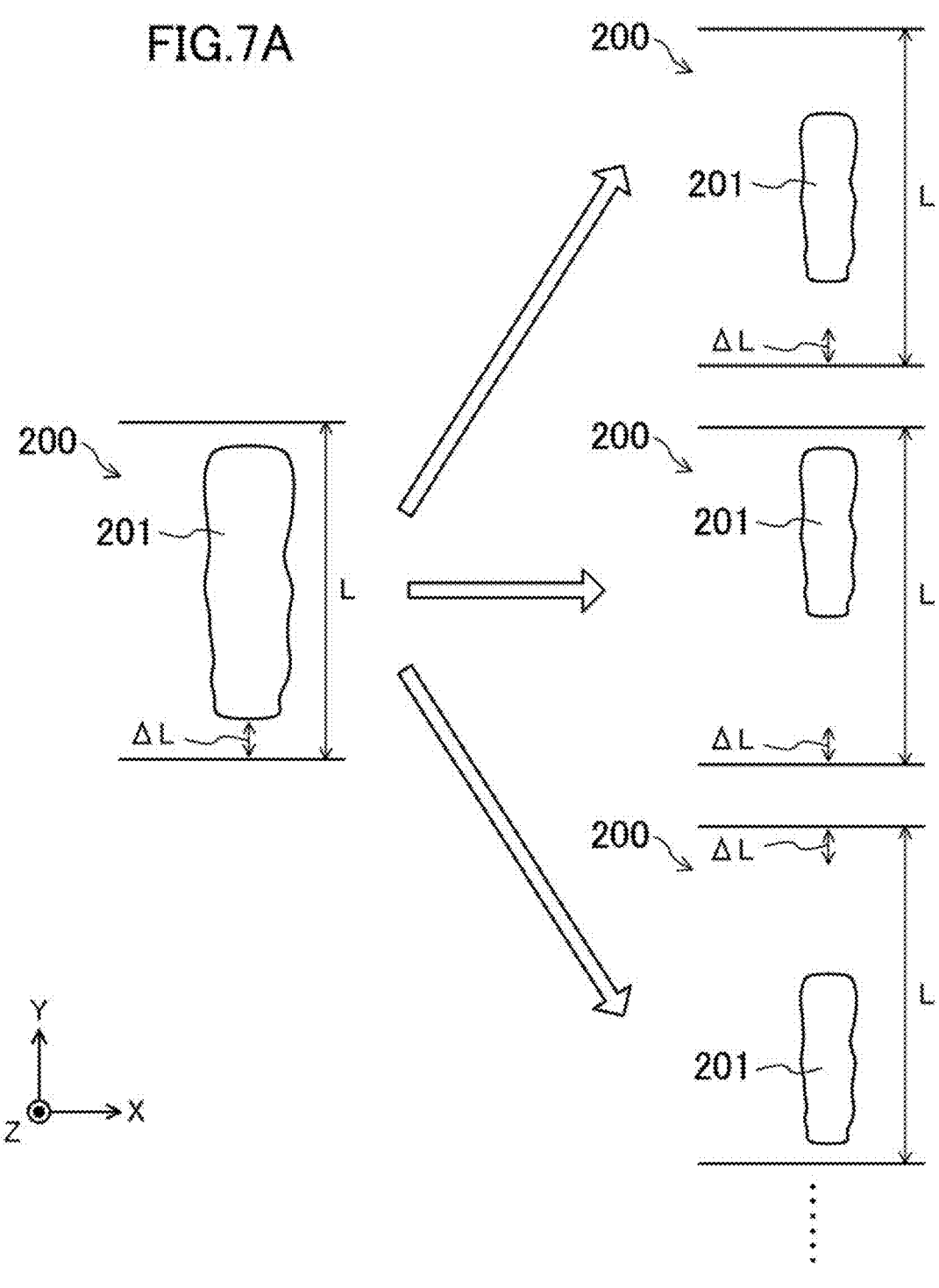
FIG. 7A is a schematic view of a first example of a procedure for generating a first learning data set.
Figure 7B:
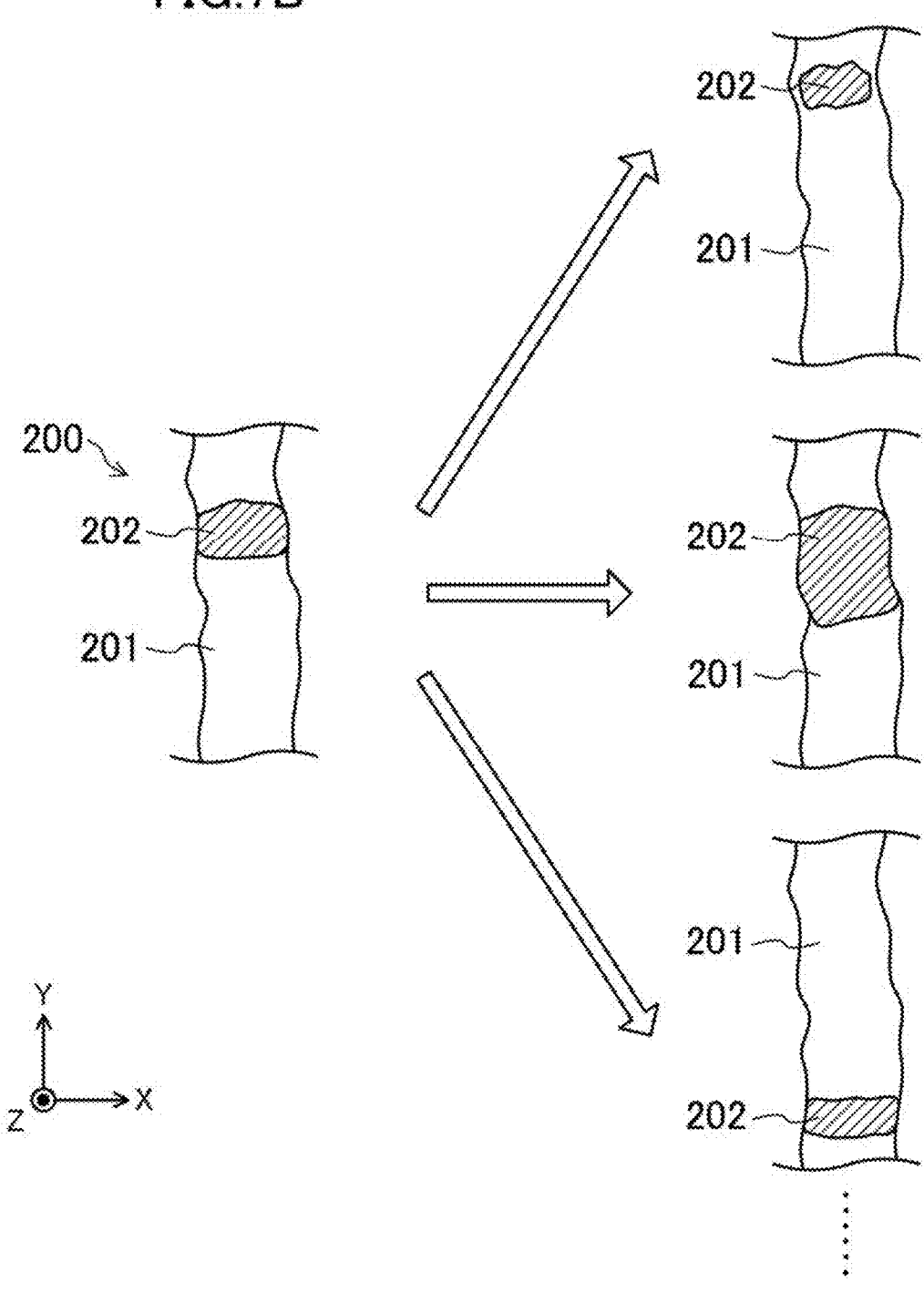
FIG. 7B is a schematic view of a second example of the procedure for generating the first learning data set.
Figure 7C:
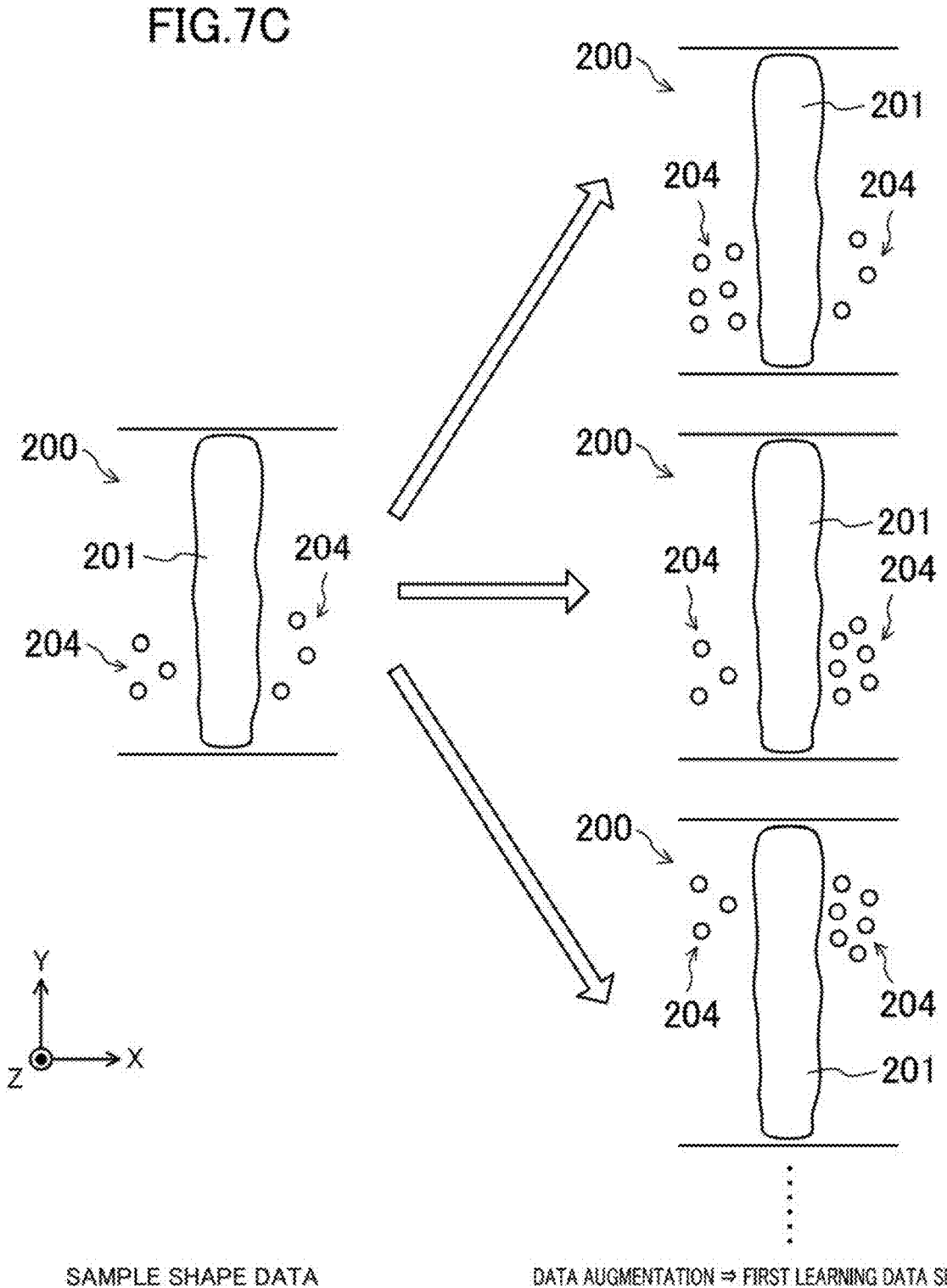
FIG. 7C is a schematic view of a third example of the procedure for generating the first learning data set.

In another example, as shown in FIG. 6B, the size and position of the hole 202 in the original sample shape data are varied to generate multiple pieces of data as the first learning data set. In this case, the height from the reference plane and the difference in height between two or more points in the weld 201 are extracted as the feature values, and are varied. In still another example, as shown in FIG. 6C, the number and position of the spatters 204 in the original sample shape data are varied to generate multiple pieces of data as the first learning data set. When similar feature values are extracted around the weld 201 and the first learning data set is generated based on the feature values, whether the spatters 204 and the smut 206 are present beyond the predetermined allowable range can be determined using the determination model generated later.

The second learning data set generator 26B changes the resolution of the first learning data set generated by the first learning data set generator 26A in several different ratios. This allows generation of a plurality of second learning data sets from one first learning data set (Step S7). The procedure for generating the second learning data sets will be further described below.

As described above, the production takt time is required to be short in some cases depending on the shape of the weld 201 by increasing the inspection speed, i.e., the scanning speed of the shape measurement unit 21, to acquire the shape data with the resolution in the direction along the welding line increased. In other cases, for accurate detection of small shape defects, the scanning speed of the shape measurement unit 21 is kept low to acquire the shape data with the resolution in the direction along the welding line lowered.

For the acquisition of the sample shape data, the conditions for the inspection are fixed. That is, the measurement resolution, measurement frequency, and scanning speeds in the X direction and the Y direction of the shape measurement unit 21 are fixed to predetermined values. In such a case, the data density and resolution of the first learning data set generated based on the sample shape data reflect the data density and resolution of the sample shape data. That is, the sample shape data and the first learning data set basically have the same data density and the same resolution. The second learning data set obtained by the data augmentation on the first learning data set also has the same data density and the same resolution as the sample shape data.

In this case, as described above, the shape of the weld 201 may not be correctly evaluated if the shape data having a greatly different data density or resolution is inputted to the determination model generated based on the second learning data set.

Thus, according to the present embodiment, the data density or resolution of the first learning data set is changed in different ways to generate multiple pieces of data as the second learning data set which is a group of learning data required to generate a new determination model. This allows the generation of a desired determination model without changing the inspection conditions to acquire a large amount of sample shape data.

Figure 8A:
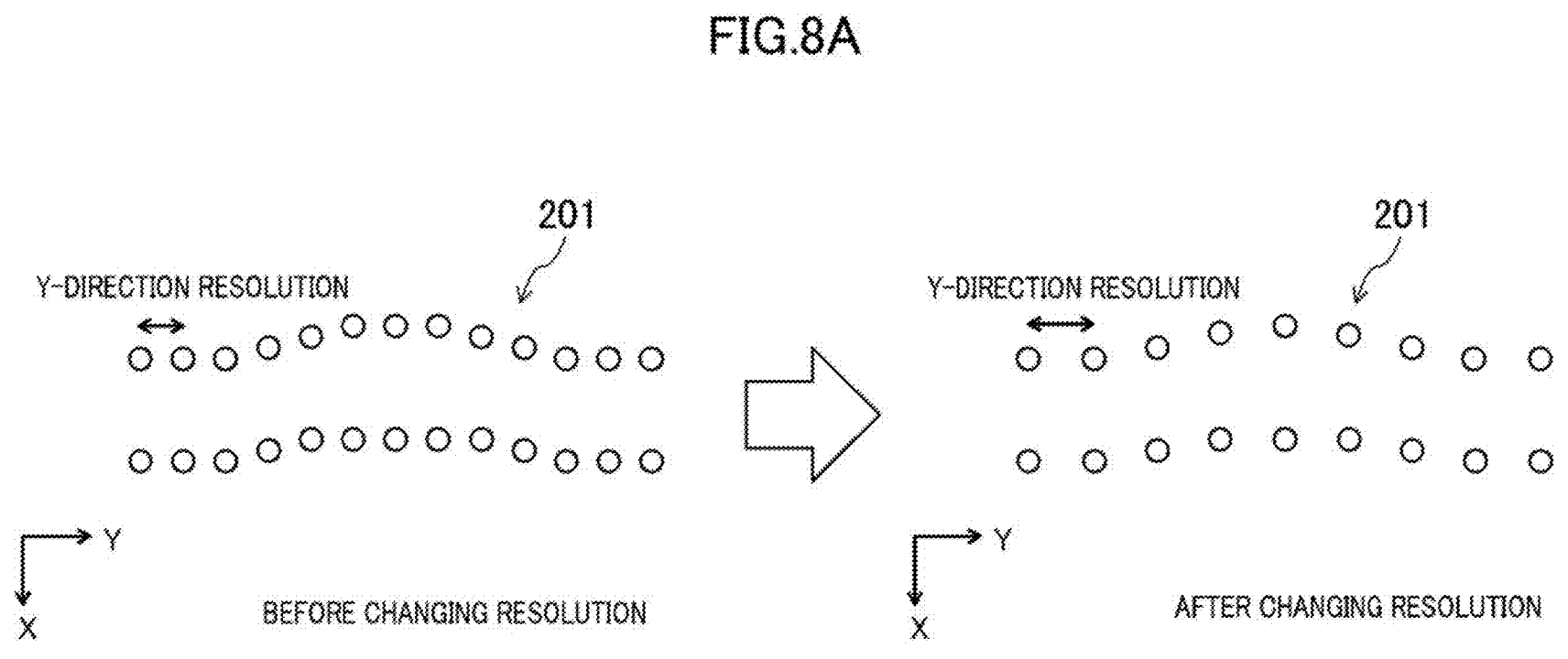
Figure 8B:
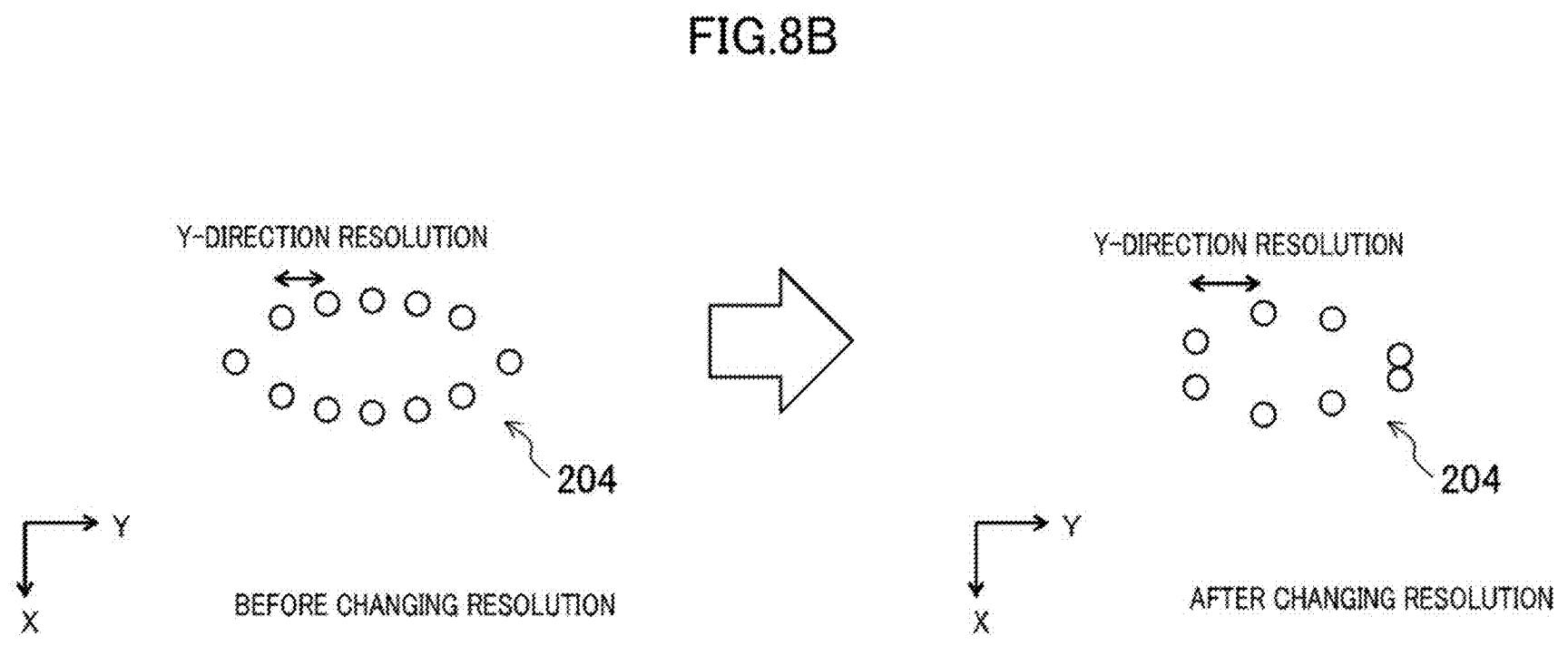

For example, the second learning data set is generated by changing the resolution in the Y direction. As shown in FIG. 8A, if the shape of the first learning data set reflects a weld bead extending in the Y direction and including a curved part, the outline of the second learning data set after the resolution is changed is not greatly different from the outline of the first learning data set. On the other hand, as shown in FIG. 8B, if the shape of the first learning data set reflects a substantially elliptical spatter 204, the outline of the second learning data set after the resolution is changed is greatly different from the outline of the first learning data set. In practice, the resolution of the first learning data set is changed by a method similar to the conversion/correction of the resolution described later.

The second learning data set may be generated by changing the data density. In many cases, data is thinned at predetermined intervals in the first learning data set to reduce the data density, thereby generating the second learning data set.

In general, acquisition of the sample shape data requires reliable acquisition of the shape and feature values of the target. Thus, the shape measurement is often performed at a higher measurement frequency or a lower scanning speed. However, this measurement takes a long inspection time, and the scanning speed is often increased to shorten the inspection time for shorter production takt time in an actual processing site.

If the resolution is changed as described above in this case, the amount of calculation for converting the coordinate points increases, placing a greater load on the CPU 23a or other components. The calculation also takes time, which is unsuitable for generating a large number of second learning data sets. Thus, the data density is lowered instead of changing the resolution to generate the second learning data set.

Figure 8C:
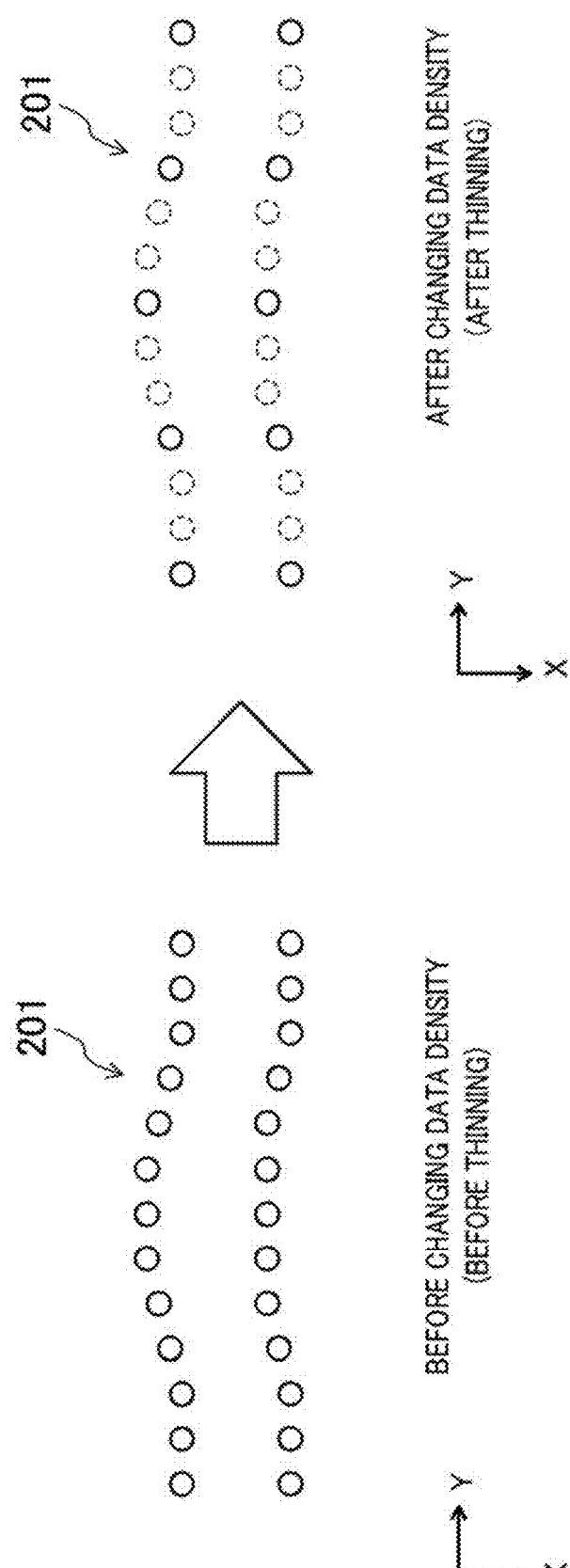
FIG. 8C is a schematic view of a third example of the procedure for generating the second learning data set.
Figure 8D:
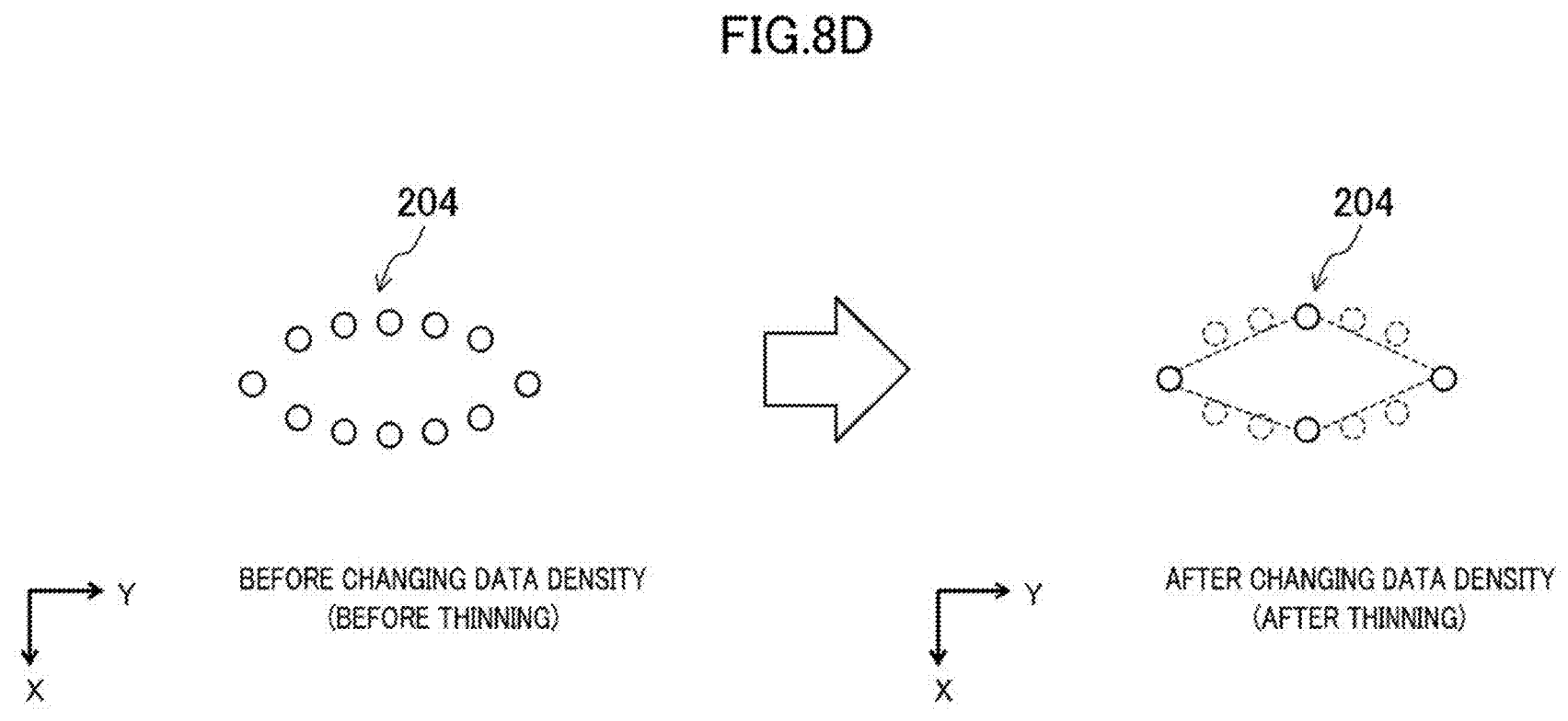

In the example shown in FIGS. 8C and 8D, the second learning data set is generated by extracting data every third point in the Y direction and thinning out the remaining points. However, the interval of data thinning is not particularly limited to this example. The shape of the first learning data set shown in FIG. 8C before the resolution is changed corresponds to the shape of the first learning data set shown in FIG. 8A. The shape of the first learning data set shown in FIG. 8D before the resolution is changed corresponds to the shape of the first learning data set shown in FIG. 8B.

In FIG. 8C, the outline of the second learning data set having the data density changed does not greatly vary from the outline of the first learning data set, as in the example shown in FIG. 8A. In FIG. 8D, the outline of the second learning data set having the data density changed greatly varies from the outline of the first learning data set, as in the example shown in FIG. 8B. In particular, in the example shown in FIG. 8D, the data density is changed to alter the outline of the spatter 204 from a substantially elliptical shape to a rhombic shape. Thus, the shape of the second learning data set may differ from the shape of the original sample shape data or the first learning data set due to the change in the resolution or the data density. This corresponds to the change in the scanning speed or any other value between the time of acquiring the sample shape data and the time of actual appearance inspection. In other words, the shape of the second learning data set is corrected to match the shape of the weld 201 acquired at the actual inspection by changing the resolution or data density of the first learning data set.

[Procedure for Weld Appearance Inspection]

Figure 10A:
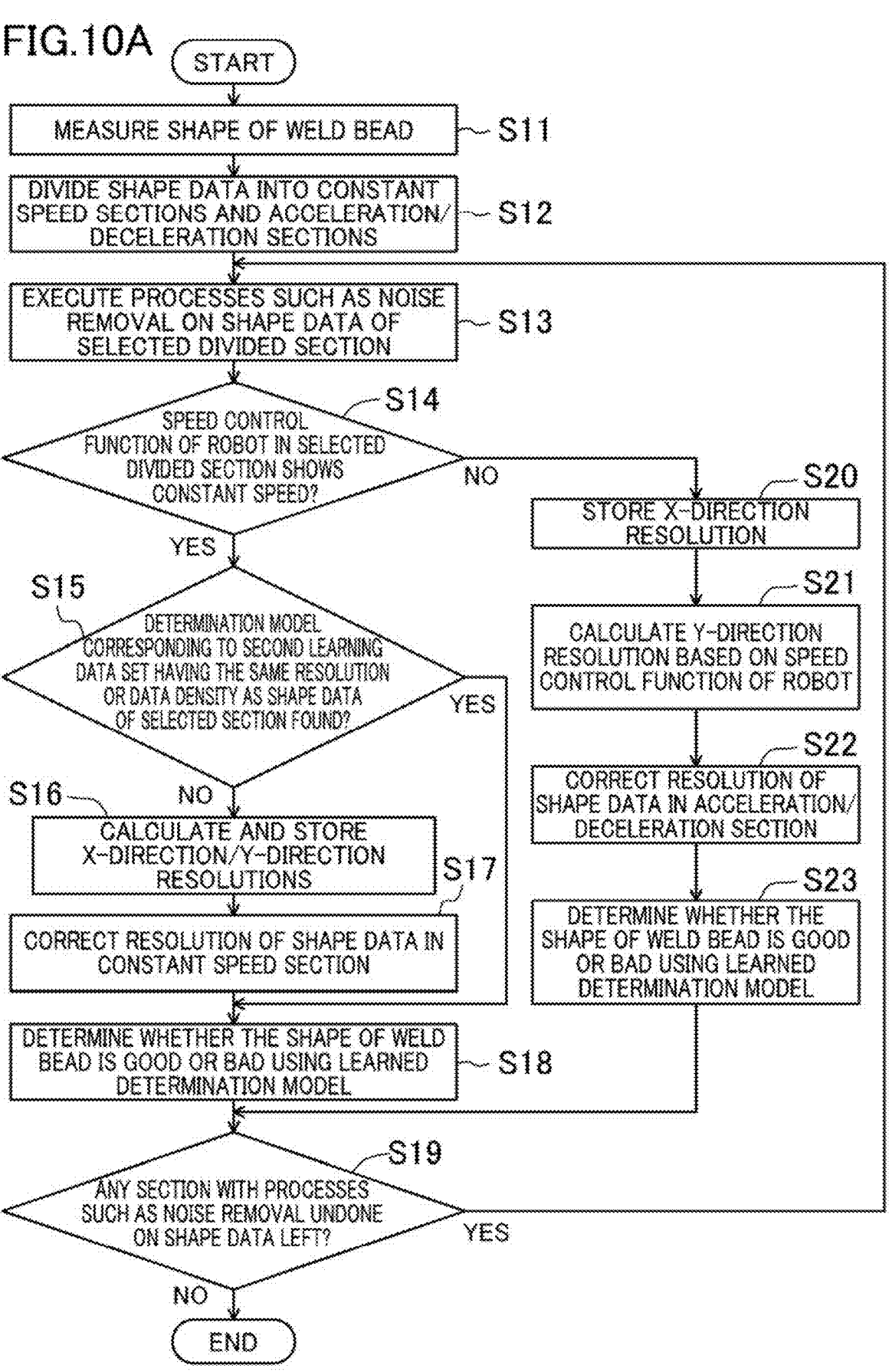
FIG. 10A is a flowchart of a procedure for weld appearance inspection.
Figure 10B:
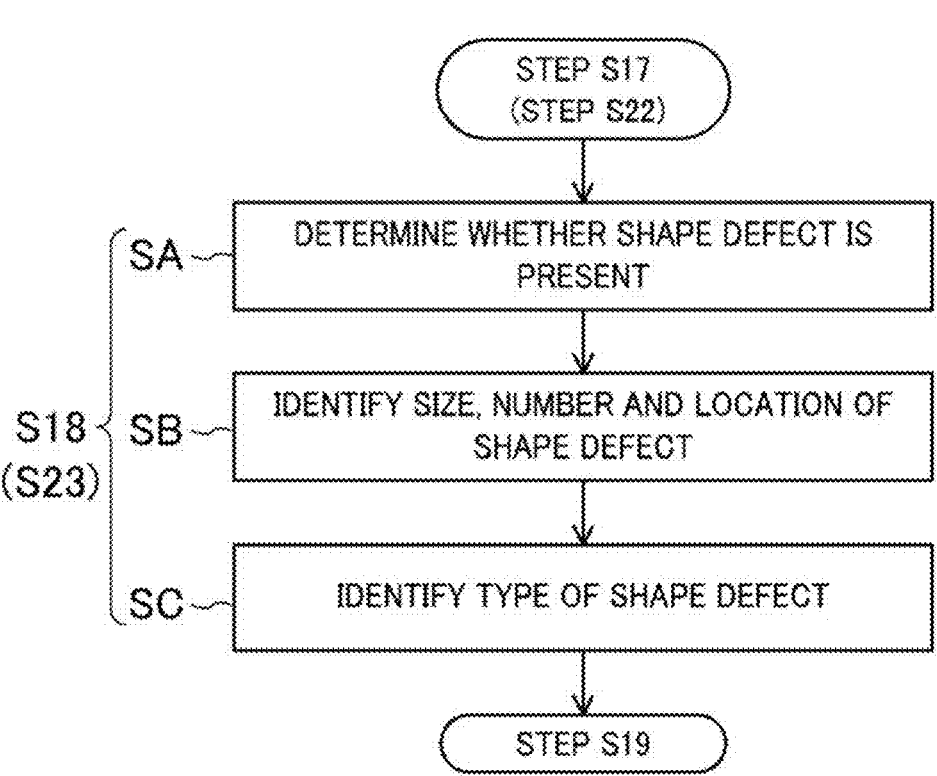
FIG. 10B is a flowchart of a procedure for determining whether the shape of a weld bead is good or bad.

FIG. 10A is a flowchart of a procedure for weld appearance inspection, and FIG. 10B is a flowchart of a procedure for determining whether the shape of a weld bead is good or bad.

Steps S11 to S13 are the same as Steps S1 to S3 shown in FIG. 9, and will not be described below. In Step S13, the shape data processor 24 performs the above-described processes such as edge enhancement correction and noise removal on the shape data of the section selected from the sections divided in Step S12 (this section will be hereinafter referred to as a selected section).

Next, the data processor 23 determines whether the selected section for which Step S13 has been executed is the constant speed section. This determination is made based on whether the speed control function of the robot 16 in the selected section indicates a constant speed, that is, a speed that is constant with respect to time (Step S14). The speed control function of the robot 16 is transmitted from the robot controller 17 to the data processor 23 in response to a request from the data processor 23. If the determination result in Step S14 is negative, the process proceeds to Step S20.

If the determination result in Step S14 is positive, that is, the selected section is the constant speed section, the shape data processor 24 determines whether the first storage 25 stores the determination model generated based on the second learning data set having the same resolution or data density as the shape data of the selected section (Step S15). Step S15 may be executed by a functional block in the data processor 23 other than the shape data processor 24.

If the determination result in Step S15 is positive, the process proceeds to Step S18. If the determination result in Step S15 is negative, that is, no determination model generated based on the second learning data set having the same resolution or data density as the shape data of the selected section is found, the process proceeds to Step S16.

<When Selected Section is Constant Speed Section>

In Step S16, the shape data processor 24 calculates the resolution in the X direction (hereinafter referred to as an X-direction resolution) and resolution in the Y direction (hereinafter referred to as a Y-direction resolution) of the shape data acquired in Step S1, and stores the calculated resolutions in the first storage 25.

As described above, the X-direction resolution corresponds to a distance between the measurement points adjacent to each other in the X direction. In general, the scanning width of the laser beam emitted by the shape measurement unit 21 is constant. The Y-direction resolution in the constant speed section is expressed by the following Formula (1).

$$Ry = 1000 \ V/60 \ F = 50 \ V/3 \ F \qquad (1)$$

where Ry (mm) is the Y-direction resolution of the shape data in the selected section, V (m/min) is the travel speed of the robot 16, and F (Hz) is the measurement frequency of the shape measurement unit 21.

That is, in the Y direction, the shape is measured at every period of 1/F. In the X direction, multiple measurement points are measured at once at every period of 1/F over the scanning width of the laser beam. The X-direction resolution of the shape data is usually determined according to the size and interval of pixels of a camera which is not shown or the light receiving sensor array 21*b* in the shape measurement unit 21. This is also the case when the selected section is the constant speed section or the acceleration/deceleration section.

The measurement resolution in the X direction and measurement frequency F of the shape measurement unit 21 are transmitted from the sensor controller 22 to the data processor 23 in response to a request from the data processor 23.

After Step S16, the shape data processor 24 converts/corrects the resolution or data density of the shape data of the selected section (Step S17). As described above, the data density is mostly corrected by thinning the sample shape data or the first learning data set at a predetermined ratio. Thus, the conversion/correction of the resolution will be described in detail later.

FIG. 10 is a conceptual diagram illustrating a procedure for deriving coordinate points of the shape data in conversion/correction of the resolution. The resolution is converted/corrected by using, relative to the height in the Z direction of a predetermined coordinate point (x, y), the height in the Z direction of each of other coordinate points (x+Rx, y), (x, y+Ry), and (x+Rx, y+Ry) adjacent to the predetermined coordinate point (x, y). Rx (mm) is the X-direction resolution of the shape data in the selected section.

In the following description, the height in the Z direction at a coordinate point (x, y), i.e., Z coordinates, is represented by Z (x, y). The origin of the coordinate point (x, y) is set at, for example, the start end of the weld 201. In this case, the origin of the Z coordinates Z (x, y) is set with reference to the surface of the workpiece 200 near the start end.

The resolution is converted/corrected by the following procedure. First, as shown in Formulae (2) and (3), an X-direction resolution coefficient Cx and a Y-direction resolution coefficient Cy are calculated.

$$Cx = Rx/Rx_0 \tag{2}$$

$$Cy = Ry/Ry_0 \tag{3}$$

where $Rx_0$ is the X-direction resolution of the sample shape data, and Ryo is the Y-direction resolution of the sample shape data. The X-direction resolution $Rx_0$ and the Y-direction resolution Ryo are stored in the first storage 25 in advance.

Next, for each of the XY coordinates reconstructed with the resolution at the acquisition of the sample shape data, Z (Xn/Cx, Ym/Cy) is calculated as the Z coordinates to satisfy Formula (4).

$$Z(Xn/Cx, Ym/Cy) = \tag{4}$$

$$(1 - dx) \times (1 - dy) \times Z(x, y) + dx \times (1 - dy) \times Z(x + Rx, y) +$$

$$(1 - dx) \times dy \times Z(x, y + Ry) + dx \times dy \times Z(x + Rx, y + Ry)$$

where n is a variable corresponding to each point of the point group data in the X direction, is an integer, and satisfies $1 \le n \le N$ (N is the number of point groups in the X direction), m is a variable corresponding to each point of the point group data in the Y direction, is an integer, and satisfies $1 \le m \le M$ (M is the number of point groups in the Y direction), dx is a value obtained by dividing the distance in the X direction between the coordinate point (x, y) and the coordinate point (Xn/Cx, Ym/Cy) by the distance in the X direction between the coordinate point (x, y) and the coordinate point (x+Rx, y), and dy is a value obtained by dividing the distance in the Y direction between the coordinate point (x, y) and the coordinate point (Xn/Cx, Ym/Cy) by the distance in the Y direction between the coordinate point (x, y) and the coordinate point (x, y+Ry).

Figure 11:
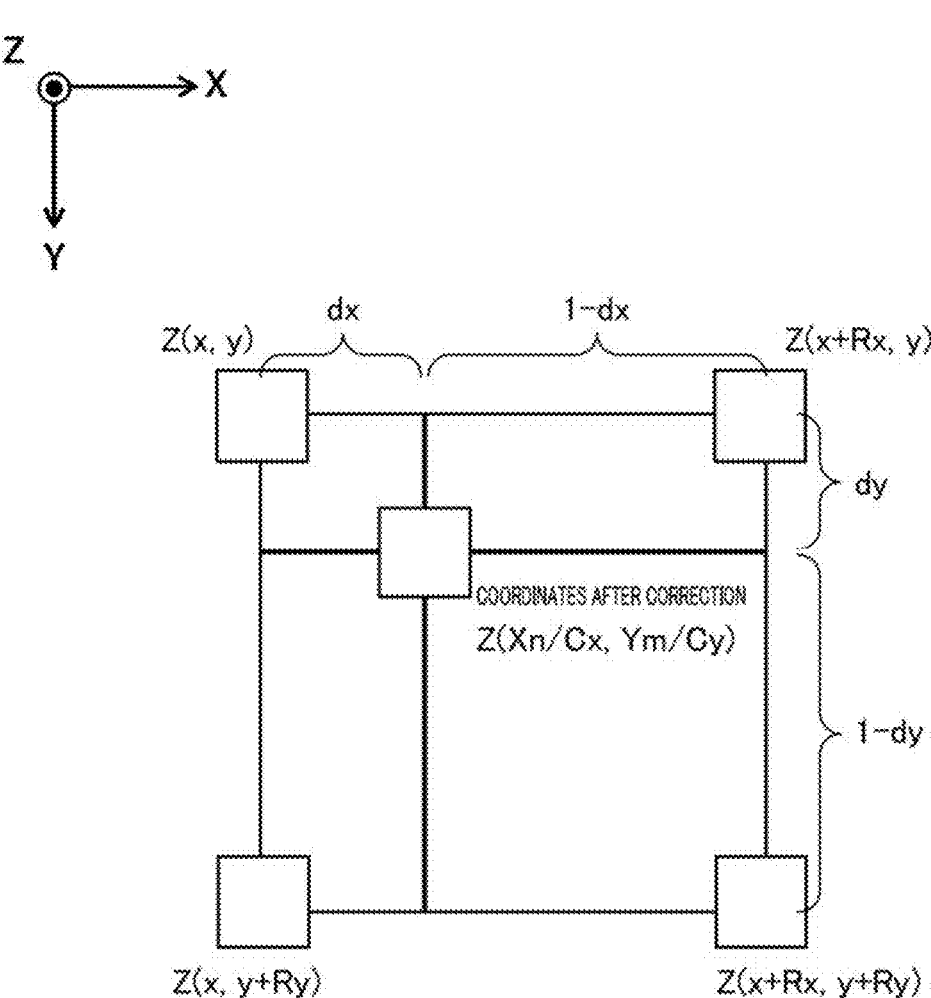
FIG. 11 is a conceptual diagram illustrating a procedure for deriving coordinate points of shape data in conversion/correction of a resolution.

That is, the ratio of dx to (1-dx) shown in FIG. 11 is the ratio of the distance in the X direction between the coordinate point (x, y) and the coordinate point (Xn/Cx, Ym/Cy) to the distance in the X direction between the coordinate point (x+Rx, y) and the coordinate point (Xn/Cx, Ym/Cy). Likewise, the ratio of dy to (1-dy) is the ratio of the distance in the Y direction between the coordinate point (x, y) and the coordinate point (Xn/Cx, Ym/Cy) to the distance in the Y direction between the coordinate point (x, y+Ry) and the coordinate point (Xn/Cx, Ym/Cy).

The height in the Z direction at the coordinate point (Xn/Cx, Ym/Cy) is derived based on the heights in the Z direction at four points around the coordinate point (Xn/Cx, Ym/Cy), that is, the coordinate points (x, y), (x+Rx, y), (x, y+Ry), and (x+Rx, y+Ry) before reconstruction.

Z (Xn/Cx, Ym/Cy) as the coordinates after the correction shown in Formula (4) is calculated for all the point groups in the selected section, and thus, the conversion/correction of the resolution of the shape data is completed.

The process of Step S17 corrects the resolution of the shape data to the same value as the resolution of the sample shape data stored in the first storage 25. That is, the first storage 25 stores a determination model generated based on the sample shape data having the same resolution as the corrected shape data.

After Step S17 is executed, the process proceeds to Step S18, and the first determination unit 28 determines whether the shape of the weld 201 in the selected section is good or bad using the shape data after the conversion/correction of the resolution. Details of Step S18 will be described later.

After Step S18 is executed, the data processor 23 determines whether any section where the process of Step S13 is unexecuted is present among the divided sections of the shape data (Step S19).

If the determination result of Step S19 is positive, the process returns to Step S13. Then, the section where the process of Step S13 is unexecuted is selected, the process of Step S13 is executed, and the series of steps are repeated until the determination result of Step S19 turns to be negative.

If the determination result in Step S19 is negative, the shape data of the measured weld bead has no section where the preprocessing such as the noise removal is unexecuted, that is, no divided section where the shape evaluation is unexecuted is left. Thus, the appearance inspection of the weld 201 ends.

<When Selected Section is Acceleration/Deceleration Section>

If the determination result in Step S14 is negative, that is, the selected section is the acceleration/deceleration section, the data processor 23 acquires the X-direction resolution of the shape data acquired in Step S11 from the sensor controller 22 and stores the acquired resolution in the first storage 25 (Step S20).

Next, the shape data processor 24 calculates the Y-direction resolution of the shape data acquired in Step S11 based on the speed control function of the robot 16 (Step S21). The speed control function of the robot 16 is transmitted from the robot controller 17 to the shape data processor 24 of the data processor 23 in response to a request from the data processor 23. The speed control function of the robot 16 may be temporarily transmitted to and stored in the first storage 25, and then transmitted to the shape data processor 24.

Further, the shape data processor 24 performs the conversion/correction of the resolution of the shape data of the selected section (Step S22).

Figure 12:
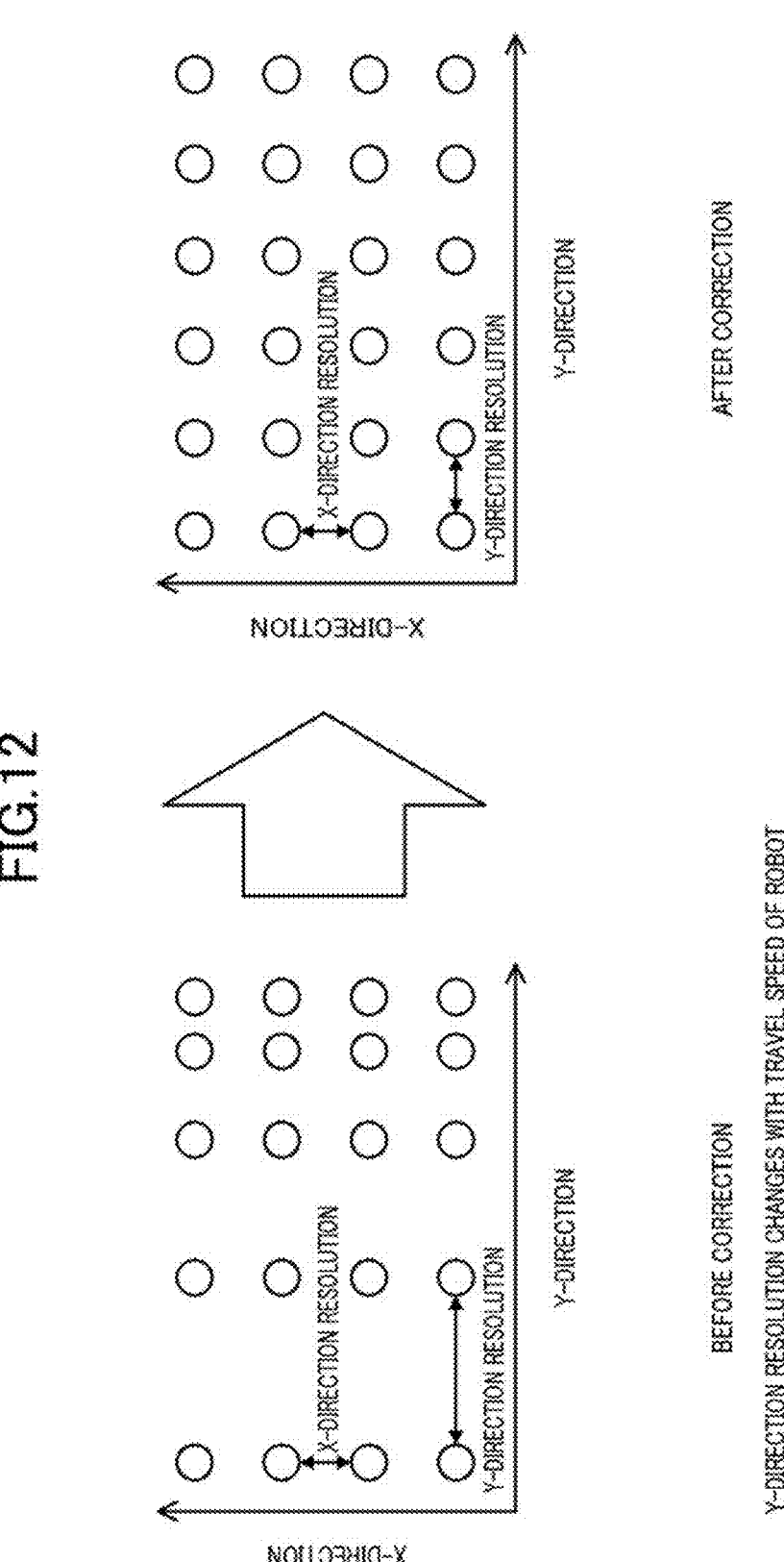
FIG. 12 is a conceptual diagram illustrating how the positions of coordinate points in the shape data change before and after conversion/correction of a resolution in an acceleration/deceleration section.
Figure 13:
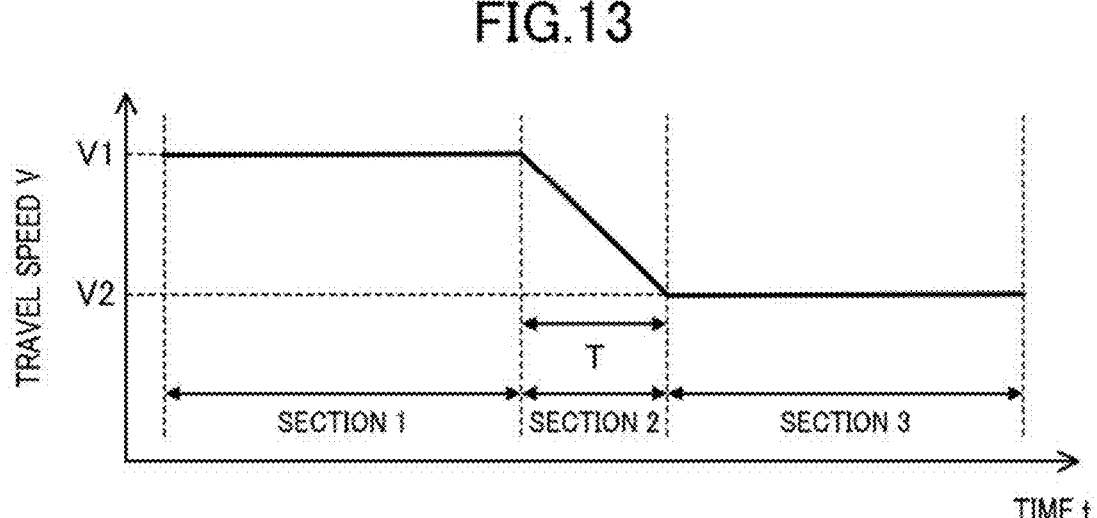
FIG. 13 is a schematic view of an example of a speed control function of a robot in the acceleration/deceleration section.

The resolution of the shape data at the time of acceleration or deceleration, particularly the Y-direction resolution, will be described with reference to FIGS. 12 and 13. FIG. 12 is a conceptual diagram illustrating how the positions of the coordinate points in the shape data change before and after the conversion/correction of the resolution in the acceleration/deceleration section. FIG. 13 is a schematic view of an example of the speed control function of the robot in the acceleration/deceleration section.

In general, for the appearance inspection of one weld 201, the scanning frequency and scanning width of the laser beam are rarely changed. As described above, when the direction along the welding line is the Y direction, the X direction is a direction intersecting with the direction along the welding line. The laser beam of the shape measurement unit 21 for measuring the shape travels in the Y direction at the travel speed of the tip of the robot 16 (hereinafter, simply referred to as the travel speed of the robot 16) to periodically scan the weld in the X direction across the welding line. Thus, the X-direction resolution Rx of the shape data can be considered to be constant in many cases in each of the constant speed section and the acceleration/deceleration section.

The Y-direction resolution Ry changes in accordance with the travel speed V of the robot 16. When the selected section is the constant speed section, the measurement frequency F and the travel speed V are constants, and the Y-direction resolution Ry is also a constant as is clear from Formula (1).

When the selected section is the acceleration/deceleration section, for example, when the robot 16 is traveling at an accelerating speed, the interval in the Y direction between the measurement points adjacent to each other increases with time. When the robot 16 is traveling at a decelerating speed, the interval in the Y direction between the measurement points adjacent to each other decreases with time. As a result, for example, as shown in the left graph in FIG. 12, the Y-direction resolution changes between the adjacent measurement points in the Y direction. When the shape of the weld 201 is evaluated based on such point group data (shape data), an accurate result cannot be obtained.

Thus, when the selected section is the acceleration/deceleration section, the Y-direction resolution needs to be corrected to a form corresponding to the speed control function of the robot 16. Specifically, the Y-direction resolution Ry (t) (mm) is expressed as shown in Formula (5).

$$Ry(t) = 1000 \; V(t)/60 \; F = (50/3F) \times V(t) \tag{5}$$

where V (t) (m/min) is the speed control function of the robot 16, and F (Hz) is the measurement frequency of the shape measurement unit 21. As will be described later, V (t) is described by a k-th order function (k is an integer of one or more) of time t (sec).

A resolution coefficient $Cy_m$ (t) at the m-th coordinate point in the Y direction from the origin is expressed by Formula (6).

[Math 1]

$$Cy_m(t) = \int_0^{Tm} \left( \frac{Ry(t)}{n \times Ry0} \right) dt \tag{6}$$

where Tm is time taken to travel from the origin to the m-th coordinate point.

Next, the Z coordinates as the coordinates after the correction are calculated to satisfy Formula (7) for each point of the XY coordinates reconstructed with the resolution at the acquisition of the sample shape data.

$$Z(Xn/Cx, \; Ym/Cy_m(t)) = \tag{7}$$
$$(1 - dx) \times (1 - dy) \times Z(x, \; y) + dx \times (1 - dy) \times Z(x + Rx, \; y) +$$
$$(1 - dx) \times dy \times Z(x, \; y + Ry) + dx \times dy \times Z(x + Rx, \; y + Ry)$$

Formula (7) is the same as Formula (4) except that the reconstructed Y coordinates $Ym/Cy_m$ (t) are described as the function of time t.

$Z (Xn/Cx, \; Ym/Cy_m$ (t)) shown in Formula (7) is calculated for all the point groups included in the selected section, and the conversion/correction of the resolution of the shape data is completed.

The process of Step S22 corrects the resolution of the shape data to the same value as the resolution of the sample shape data stored in the first storage 25. That is, the first storage 25 stores a determination model generated based on the sample shape data having the same resolution as the corrected shape data.

After Step S22 is executed, the process proceeds to Step S23, and the first determination unit 28 determines whether the shape of the weld 201 in the selected section is good or bad using the shape data after the conversion/correction of the resolution. Details of Step S23 will be described later.

After Step S23 is executed, the data processor 23 determines whether any section where the process of Step S3 is unexecuted is present among the divided sections of the shape data (Step S19).

If the determination result of Step S19 is positive, the process returns to Step S13. Then, the section where the process of Step S13 is unexecuted is selected, the process of Step S13 is executed, and the series of steps are repeated until the determination result of Step S19 turns to be negative.

If the determination result in Step S19 is negative, no divided section where the shape evaluation is unexecuted is present. Thus, the appearance inspection of the weld 201 ends.

As shown in FIG. 13, an example in which the shape data is divided into three sections (sections 1 to 3) will be described.

As is apparent from FIG. 13, the section 1 and the section 3 are the constant speed sections. Thus, the appearance of the weld 201 is inspected by executing Steps S11 to S18 of FIG. 10A.

The section 2 is the deceleration section. Specifically, the travel speed V (m/min) of the robot 16 monotonously decreases from V1 to V2 (<V1) in period T (sec). Thus, the speed control function V (t) of the robot 16 in the section 2 is expressed in the form shown in Formula (8)

$$V(t) = A \times t + B = \left((V2 - V1)/T\right) \times t + V1 \qquad (8)$$

Specifically, the speed control function V (t) is a linear function of time t, a linear coefficient A of time t is (V2-V1)/T, and a constant B is V1.

In this case, the data processor 23 acquires various types of information characterizing the speed control function V (t) from the robot controller 17. For example, when the speed control function V (t) is a k-th order function (k is an integer of one or more) of time t, each coefficient value of t to $t^k$ and the value of the constant B are acquired. In the section 2, the appearance inspection of the weld 201 is performed by executing Steps S1 to S4 and S20 to S23 in FIG. 10A.

<Procedure for Determining Whether Shape of Weld Bead is Good or Bad>

A procedure for determining whether the shape of the weld bead (the weld 201) is good or bad shown in FIG. 10B includes the same processes as Steps S18 and S23 of FIG. 10A, and will be described together.

Each of Steps S18 and S23 in FIG. 10A is divided into sub steps SA to SC shown in FIG. 10B. First, the first determination unit 28 determines whether the shape data in the selected section includes a shape defect (sub step SA). A determination model used in this step is previously reinforced by learning using the second learning data set as described above.

The first determination unit 28 identifies the size and number of the shape defects and the location of each shape defect in the weld 201 (sub step SB). Further, the first determination unit 28 identifies the type of the shape defect (sub step SC).

In the sub step SC, as described above, the type of the shape defect is identified in consideration of the shape and size of the shape defect and the location of the shape defect in the weld 201. In this case, for example, the probability that the shape defect is the spatter 204 is calculated, and the shape defect is identified as the spatter 204 if the probability is equal to or higher than a predetermined value (e.g., 70%).

The final result of the determination of the shape of the weld 201 is transmitted to the notification unit 29 or the display 23g. If the shape is determined to be bad, the shape data acquired by the shape measurement unit 21, i.e., the shape of the weld 201, is displayed on the display 23g as point group data.

When all the welds 201 included in one workpiece 200 are determined to be good, the workpiece 200 is determined to be a non-defective product and is sent to the subsequent process or is shipped as a non-defective product.

Several measures can be taken when a defect is found in one or more welds 201 included in one workpiece 200. For example, after the appearance inspection of all the welds 201 included in the workpiece 200, the inspection result is stored, and the workpiece 200 is discarded as a defective product. In this case, the inspection result is stored in, for example, the first storage 25 of the data processor 23. However, the present invention is not limited to this example. When the defect is found in the weld 201, the workpiece 200 may be discarded as a defective product.

For example, after the appearance inspection of all the welds 201 included in the workpiece 200, the inspection result may be stored, and the workpiece 200 may proceed to a repair process. In the repair process, the weld 201 determined to be defective is rewelded.

For example, after the appearance inspection of all the welds 201 included in the workpiece 200, the inspection result may be stored, and the welder may visually check the defective welds 201 again. Whether the weld 201 is repairable is determined by the visual check. If the workpiece 200 is determined to be repairable, the workpiece 200 proceeds to the repair process, and the defective weld 201 is rewelded.

[Advantages]

As described above, the appearance inspection apparatus 20 of the present embodiment inspects the appearance of the weld 201 of the workpiece 200.

The appearance inspection apparatus 20 is attached to the robot 16 and includes at least the shape measurement unit 21 configured to measure the three-dimensional shape of the weld 201 along a welding line and the data processor 23 configured to process the shape data acquired by the shape measurement unit 21.

The data processor 23 includes at least the shape data processor 24 configured to perform at least noise removal from the sample shape data acquired in advance by the shape measurement unit 21. The data processor 23 further includes the first learning data set generator 26A configured to generate a plurality of first learning data sets based on the sample shape data and the second learning data set generator 26B configured to generate a plurality of second learning data sets based on each of the plurality of first learning data sets. The data processor 23 further includes the determination model generator 27 configured to generate multiple types of determination models for determining whether the shape of the weld 201 is good or bad using the plurality of second learning data sets. The data processor 23 further includes the first determination unit 28 configured to determine whether the shape of the weld 201 is good or bad based on the shape data processed by the shape data processor 24 and the determination models generated by the determination model generator 27.

The first learning data set generator 26A generates the plurality of first learning data sets by performing data augmentation on the sample shape data. The second learning data set generator 26B generates the plurality of second learning data sets by changing the data density or resolution of each of the plurality of first learning data sets in different conversion ratios.

The appearance inspection apparatus 20 configured as described above can accurately evaluate the three-dimensional shape of the weld 201 and can correctly determine whether the shape of the weld 201 is good or bad, although the inspection conditions are changed according to the production takt time and the required inspection accuracy.

A single workpiece 200 usually includes a large number of welds 201. In this case, the workpiece 200 often includes various types of welds 201 having different shapes, and the inspection conditions are changed as appropriate in accordance with the shapes of the welds 201.

According to the present embodiment, although one workpiece 200 includes the welds 201 having different inspection conditions, the three-dimensional shape of each weld 201 can be accurately evaluated, and whether the shape of the weld 201 is good or bad can be correctly determined.

In particular, according to the present embodiment, the data density or resolution of one first learning data set is changed in different conversion ratios to generate the plurality of second learning data sets. Further, the determination model is generated for each of the second learning data sets generated.

Thus, the determination model generated based on the second learning data set having the suitable data density or resolution can be selected, although the conditions for the actual inspection of the weld 201 are different from the inspection conditions at the time of acquiring the sample shape data. This allows the generation of a desired determination model without acquiring a large amount of sample shape data by changing the inspection conditions.

The workpiece 200 does not always have a single weld 201, but often includes various types of weld beads of different shapes. In this case, the inspection conditions are set for each of the types of welds 201 in accordance with the shape of each weld 201.

According to the present embodiment, the determination model generated based on the second learning data set having the suitable data density or resolution can be selected, although different inspection conditions are set for the appearance inspection of the different welds 201. This allows the generation of a desired determination model without acquiring a large amount of sample shape data by changing the inspection conditions.

The determination model used by the first determination unit 28 is generated based on the second learning data set having a resolution closest to the resolution of the shape data acquired by the shape measurement unit 21. Alternatively, the determination model used by the first determination unit 28 is generated based on the second learning data set having a data density closest to the data density of the shape data acquired by the shape measurement unit 21.

This allows accurate evaluation of the three-dimensional shape of the weld 201 and correct determination of whether the shape of the weld 201 is good or bad.

The appearance inspection apparatus 20 further includes the sensor controller 22 configured to store conditions for the inspection of the weld 201 by the shape measurement unit 21 and transmit the stored inspection conditions to the data processor 23. When the direction along the welding line is the Y direction, the sensor controller 22 transmits the measurement resolution in the X direction intersecting with the Y direction and the Z direction which is the height direction of the weld 201 and the measurement frequency to the data processor 23.

The data processor 23 receives the travel speed V of the robot 16 or the speed control function V (t) of the robot 16 from the robot controller 17 configured to control the motion of the robot 16.

Thus, the resolution of the shape data can be converted/corrected easily and accurately.

The data processor 23 further includes the first storage 25 configured to store at least the sample shape data, the first learning data sets, the second learning data sets, and the determination models. With the provision of the first storage 25, the generation of the first and second learning data sets and the subsequent generation of the determination models can be smoothly performed.

The shape data processor 24 corrects the resolution of the shape data acquired by the shape measurement unit 21 when the resolution of the shape data is different from any of the resolutions of the second learning data sets stored in the first storage 25. When the shape data includes the acceleration/deceleration section, the resolution of the shape data in the acceleration/deceleration section is also considered to be different from the resolutions of the second learning data sets stored in the first storage 25.

Specifically, the shape data processor 24 corrects the resolution of the shape data acquired by the shape measurement unit 21 based on the conditions for the inspection of the weld 201 by the shape measurement unit 21 so that the resolution has the same value as the resolution of any of the second learning data sets. The inspection conditions are, for example, the measurement resolution, measurement frequency, and scanning speed of the shape measurement unit 21. As described above, the scanning speed of the shape measurement unit 21 corresponds to the scanning speed of the laser beam in the X direction, the travel speed V of the robot 16, or the speed control function V (t) of the robot 16.

The sample shape data is acquired at the measurement resolution, measurement frequency, and scanning speed of the shape measurement unit 21 that are determined in advance as described above. The determination model is reinforced by learning based on each of the plurality of second learning data sets. The second learning data sets are generated based on the first learning data set, and by extension on the sample shape data which is shape data experimentally acquired in advance before welding the actual workpiece 200. The resolution of the shape data is corrected to the same value as the resolution of the second learning data set. In this manner, the shape defects included in the second learning data set, and by extension in each of the sample shape data and the shape data, such as the hole 202 and the spatter 204, can have shape features matched. Thus, whether the shape of the weld 201 is good or bad can be determined reliably and accurately using the learned determination model.

The shape data processor 24 corrects the value of the shape data in the Z direction based on the X-direction resolution and Y-direction resolution of the shape data when the resolution of the shape data acquired by the shape measurement unit 21 is different from any of the resolutions of the second learning data sets stored in the first storage 25.

When the shape measurement unit 21 measures the three-dimensional shape of the weld 201 while the robot 16 is traveling along the welding line at a constant speed, the Y-direction resolution is determined based on the measurement frequency of the shape measurement unit 21 and the travel speed V of the robot 16.

When the shape measurement unit 21 measures the three-dimensional shape of the weld 201 while the robot 16 is traveling at an accelerating speed, a decelerating speed, or both the accelerating and decelerating speeds in a predetermined section along the welding line, the Y-direction resolution is determined based on the measurement frequency F of the shape measurement unit 21 and the speed control function V (t) of the robot 16. The speed control function V (t) is described by a k-th order function of time t. However, the present invention is not limited to this example, and the speed control function V (t) may be, for example, a sine wave function or a cosine wave function. That is, the speed control function V (t) is a function depending on time t.

Thus, the resolution of the shape data can be easily and accurately converted/corrected although the scanning speed of the shape measurement unit 21 is changed in various ways.

The first learning data set generator 26A classifies the multiple pieces of sample shape data acquired in advance by the shape measurement unit 21 by material and shape of the workpiece 200, and performs data augmentation on the classified pieces of sample shape data to generate a plurality of first learning data sets.

The determination model generator 27 generates a determination model for each material and shape of the workpiece 200 using the plurality of second learning data sets.

With the appearance inspection apparatus 20 configured in this manner, a required number of first and second learning data sets can be generated although the amount of the sample shape data is small, and the determination model can be provided with enhanced accuracy. This allows accurate determination of whether the shape of the weld 201 is good or bad. Further, a large amount of sample shape data is no longer necessary, and the number of man-hours required for determining whether the shape is good or bad can be significantly reduced. The shape defect of the weld 201 can be automatically detected without manually setting a complicated criterion for the determination. The multiple pieces of sample shape data are classified by material and shape of the workpiece 200 prior to the generation of the first learning data sets, allowing efficient generation of the first learning data sets. The second learning data sets can be efficiently generated based on the first learning data sets.

The data processor 23 further includes the notification unit 29 configured to notify the result of the determination by the first determination unit 28.

This allows the welder or the system administrator to know in real time during the welding of the workpiece 200 whether a failure has occurred at the weld 201 or not. If necessary, measures to continue the welding of the workpiece 200 or not can be taken. This can reduce the cost of the welding process.

The first learning data set generator 26A generates the first learning data sets based on one or more feature values extracted from the sample shape data. The feature value is extracted by the shape data processor 24.

The first learning data sets are generated using the feature value extracted from the sample shape data. This can simplify the generation of the first learning data sets without deteriorating the accuracy of the determination model.

The first learning data set generator 26A performs the data augmentation by changing one or more feature values extracted from the sample shape data and/or changing the position of the shape defect in the sample shape data.

The first learning data sets are generated based on the one or more feature values extracted from the sample shape data. Thus, the first learning data sets, and the second learning data sets as well, can be generated with improved efficiency, and the number of man-hours can further be reduced. The first learning data sets can be efficiently generated by a simple process of changing the feature values and/or the position of the shape defect.

The first learning data set generator 26A may classify the multiple pieces of sample shape data by inspection item for the weld 201, and may perform the data augmentation on the classified pieces of sample shape data to generate the plurality of first learning data sets.

The determination model generator 27 may generate the determination model for determining whether the shape of the weld 201 is good or bad for each inspection item of the weld 201 using the plurality of second learning data sets.

The first learning data set generator 26A may classify each of the multiple pieces of sample shape data into a piece of sample shape data of a particular portion of the weld 201 in which the determination of the shape defect is more difficult than in the other portion and a piece of sample shape data of the other portion, and may separately perform the data augmentation on the pieces of sample shape data to generate the plurality of first learning data sets.

When determining whether the shape of the weld 201 is good or bad, the first determination unit 28 determines whether the inputted shape data includes the shape defect. In this determination, the first learning data sets and the second learning data sets are generated using the sample shape data including non-defective data having no shape defect and defective data having some shape defect. In the first and second learning data sets, the defective data is processed such that the type of the shape defect is identified and the shape defect is labelled with the identified type. The determination model is previously reinforced by learning using the second learning data sets.

When the shape data includes the shape defect, the first determination unit 28 identifies the number and size of the shape defects and the location of each shape defect in the weld 201 and a predetermined region around the weld 201.

The first determination unit 28 identifies the type of each shape defect. In this identification, the number and size of the shape defects and the location of each shape defect in the weld 201 are referred to. The type of the shape defect is calculated in terms of probability, and the type of the shape defect is determined when the probability is equal to or higher than a predetermined threshold. The type of the shape defect is not limited to those shown in FIGS. 6A to 6E. When the dimension of the weld 201 does not satisfy a predetermined criterion for non-defective products, it is also regarded as the shape defect. The criterion for the dimension of the non-defective product can be set in any of the X direction, the Y direction, and the Z direction.

As described above, the first determination unit 28 determines or identifies each of the plurality of items about the shape of the weld 201, and finally determines whether the shape of the weld 201 is good or bad based on the results. This allows accurate and reliable evaluation of whether the shape of the weld 201 is good or bad.

Alternatively, when generating the determination model for each material and shape of the workpiece 200 using the plurality of learning data sets, the determination model generator 27 may separately generate the determination model corresponding to the particular portion of the weld 201 and the determination model corresponding to the other portion.

This allows the determination of whether the shape defect is present and the identification of the type of the shape defect with accuracy equal to or more than a predetermined level, although in the particular portion of the weld 201 where the determination and/or the identification is more difficult than in the other portion. This allows accurate determination of whether the shape of the weld 201 is good or bad in the appearance inspection.

The welding system 100 of the present embodiment includes the welding apparatus configured to weld the workpiece 200 and the appearance inspection apparatus 20.

The welding system 100 configured in this manner can inspect the shape of the weld 201 with high accuracy and a small number of man-hours. This can reduce the cost of the welding process.

The welding apparatus 10 includes at least the welding head 11 (welding torch 11) for applying heat to the workpiece 200, the robot 16 for holding and moving the welding head 11 (welding torch 11) to a desired position, the output controller 15 for controlling the welding output of the welding head 11 (welding torch 11), and the robot controller 17 for controlling the motion of the robot 16.

When the first determination unit 28 of the appearance inspection apparatus 20 determines that the shape of the weld 201 is bad, the output controller 15 stops the welding output of the welding head 11 (welding torch 11), and the robot controller 17 stops the motion of the robot 16 or operates the robot 16 so that the welding head 11 (welding torch 11) moves to a predetermined initial position.

The welding system 100 configured in this manner can stop the next welding if the shape of the weld 201 is bad, and can reduce the frequent production of defective products. Based on the result of the determination by the first determination unit 28 acquired for each inspection item, a failed part of the welding system 100 can be presumed, and a cause of the failure can be quickly removed, shortening downtime of the welding system 100.

A method for appearance inspection of the weld 201 according to the present embodiment includes at least measuring the three-dimensional shape of the weld 201 by the shape measurement unit 21 moving together with the robot 16 to acquire sample shape data and generating a plurality of first learning data sets by the first learning data set generator 26A based on the sample shape data.

The method for the appearance inspection of the weld 201 further includes generating a plurality of second learning data sets by the second learning data set generator 26B based on the plurality of first learning data sets and generating multiple types of determination models for determining whether the shape of the weld 201 is good or bad by the determination model generator 27 using the plurality of second learning data sets.

The method for the appearance inspection of the weld 201 further includes measuring the three-dimensional shape of the weld 201 by the shape measurement unit 21 moving together with the robot 16 to acquire shape data and determining whether the shape of the weld is good or bad by the first determination unit 28 based on the shape data processed by the shape data processor 24 and the determination models generated by the determination model generator 27.

The determination models used by the first determination unit 28 are generated based on at least one of the second learning data sets having the data density closest to the data density of the shape data processed by the shape data processor 24. Alternatively, the determination models used by the first determination unit 28 are generated based on at least one of the second learning data sets having a resolution closest to the resolution of the shape data processed by the shape data processor 24.

By this appearance inspection method, the three-dimensional shape of the weld 201 can be evaluated with high accuracy, and whether the shape of the weld 201 is good or bad can be correctly determined, although the inspection conditions are changed according to the production takt time and the required inspection accuracy.

A single workpiece 200 usually includes a large number of welds 201. In this case, the workpiece 200 often includes various types of welds 201 having different shapes, and the inspection conditions are changed as appropriate in accordance with the shapes of the welds 201.

According to the present embodiment, although one workpiece 200 includes the welds 201 having different inspection conditions, the three-dimensional shape of each weld 201 can be accurately evaluated, and whether the shape of the weld 201 is good or bad can be correctly determined.

According to the present embodiment, in particular, the determination models are generated based on at least one of the second learning data sets having the data density closest to the data density of the shape data acquired by the shape measurement unit 21 and processed by the shape data processor 24. Alternatively, the determination models are generated based on at least one of the second learning data sets having a resolution closest to the resolution of the shape data acquired by the shape measurement unit 21 and processed by the shape data processor 24.

Thus, the determination model generated based on the second learning data set having the suitable data density or resolution can be selected, although the conditions for the actual inspection of the weld 201 are different from the inspection conditions at the time of acquiring the sample shape data. This allows accurate evaluation of the three-dimensional shape of the weld 201 and correct determination of whether the shape of the weld 201 is good or bad.

Each of the steps (Steps S18 and S23 in FIG. 10A) of determining whether the shape of the weld 201 is good or bad by the first determination unit 28 further includes the following sub steps.

Specifically, the sub steps include the sub step (sub step SA in FIG. 10B) of determining whether the weld 201 has the shape defect based on the shape data inputted from the shape data processor 24 and the determination model reinforced in advance by learning, the sub step (sub step SB in FIG. 10B) of identifying the number and size of shape defects and the location of each shape defect with respect to the weld 201, and the sub step (sub step SC in FIG. 10B) of identifying the type of each shape defect.

The first determination unit 28 determines whether the shape of the weld 201 is good or bad based on the results of the determination and the identification in each of the sub steps SA to SC.

This allows accurate and reliable evaluation of whether the shape of the weld 201 is good or bad.

Other Embodiments

In the example shown in FIG. 1, both of the welding torch 11 (welding head 11) and the shape measurement unit 21 are attached to the robot 16. However, the shape measurement unit 21 may be attached to a robot (not shown) different from the robot 16 to which the welding torch 11 (welding head 11) is attached. In this case, various types of data are transmitted to the data processor 23 from another robot controller (not shown) configured to control the motion of the different robot.

The first learning data set generator 26A of the embodiment classifies the sample shape data by material and shape of the workpiece 200 and performs data augmentation on the classified pieces of sample shape data to generate the first learning data sets.

However, the first learning data set generator 26A may not have the classifying function. In this case, the determination model generator 27 may not have the function of generating the determination model for each material and shape of the workpiece 200.

The function of the first learning data set generator 26A and the function of the second learning data set generator 26B may be replaced with each other. Specifically, the first learning data set generator 26A may generate multiple types of first learning data sets having the data densities or the resolutions converted in different conversion ratios based on the sample shape data. The second learning data set generator 26B may classify the first learning data sets by material and shape of the workpiece 200 and may generate the second learning data sets based on the classified first learning data sets.

The processes performed by the first learning data set generator 26A and the second learning data set generator 26B are mainly divided into the following three processes. The three processes include classification of data by material and shape of the workpiece 200, data augmentation of the original data, and changing the data density or resolution of the original data. These three processes may be implemented by different functional blocks or the same functional block. In either case, it is needless to say that the functions are implemented by running predetermined software on the hardware of the data processor 23, particularly the CPU 23a and the GPU 23b.

The appearance inspection apparatus of the present disclosure can accurately evaluate the three-dimensional shape of welds although inspection conditions are changed, and thus is particularly useful for appearance inspection of a workpiece including various types of welds.

The invention claimed is:

1. An appearance inspection apparatus for inspecting an appearance of a weld of a workpiece, the appearance inspection apparatus comprising at least:

a shape measurement unit that is attached to a robot and configured to measure a three-dimensional shape of the weld along a welding line; and a data processor configured to process sample shape data acquired by the shape measurement unit, wherein the data processor includes at least:

a shape data processor configured to perform at least removal of noise from the sample shape data acquired in advance by the shape measurement unit;

a first learning data set generator configured to generate a plurality of first learning data sets based on the sample shape data;

a second learning data set generator configured to generate, based on each of the plurality of first learning data sets, a plurality of second learning data sets, such that at least two of the second learning data sets are generated from each of the plurality of first learning data sets;

a determination model generator configured to generate multiple types of determination models for determining whether a shape of the weld satisfies a predetermined criterion using the plurality of second learning data sets; and a first determination unit configured to determine whether the shape of the weld satisfies the predetermined criterion based on the sample shape data processed by the shape data processor and the determination models generated by the determination model generator.

2. The appearance inspection apparatus of claim 1, wherein the first learning data set generator generates the plurality of first learning data sets by performing data augmentation on the sample shape data, and the second learning data set generator generates the plurality of second learning data sets by changing a data density or resolution of each of the plurality of first learning data sets in different conversion ratios.

3. The appearance inspection apparatus of claim 1, wherein the determination models used by the first determination unit are generated based on at least one of the second learning data sets having a data density closest to a data density of the sample shape data acquired by the shape measurement unit or at least one of the second learning data sets having a resolution closest to a resolution of the sample shape data acquired by the shape measurement unit.

4. The appearance inspection apparatus of claim 1, wherein the data processor further includes:

a first storage configured to store at least the sample shape data, the first learning data sets, the second learning data sets, and the determination models.

5. The appearance inspection apparatus of claim 4, further comprising:

a sensor controller configured to store a condition for inspection of the weld by the shape measurement unit and transmit the stored inspection condition to the data processor, wherein the sensor controller transmits a measurement frequency of the shape measurement unit and a measurement resolution of the shape measurement unit in an X direction intersecting with a Y direction along the welding line and a Z direction which is a height direction of the weld to the data processor, and the data processor receives a travel speed or speed control function of the robot from a robot controller configured to control a motion of the robot.

6. The appearance inspection apparatus of claim 5, wherein when the sample shape data acquired by the shape measurement unit is different in resolution from any of the plurality the second learning data sets stored in the first storage, the shape data processor corrects the resolution of the sample shape data to a same value as the resolution of any of the second learning data sets based on the measurement resolution, measurement frequency, and scanning speed of the shape measurement unit.

7. The appearance inspection apparatus of claim 6, wherein the shape data processor corrects a value of the sample shape data in the Z direction based on an X-direction resolution and a Y-direction resolution of the sample shape data, the Y-direction resolution is determined based on the measurement frequency and the travel speed of the robot when the shape measurement unit measures the three-dimensional shape of the weld while the robot travels along the welding line at a constant speed, the Y-direction resolution is determined based on the measurement frequency and the speed control function of the robot when the shape measurement unit measures the three-dimensional shape of the weld while the robot travels at an accelerating speed, a decelerating speed, or both accelerating and decelerating speeds in a predetermined section along the welding line, and the speed control function of the robot is a function dependent on time.

8. The appearance inspection apparatus of claim 1, wherein the first learning data set generator classifies multiple pieces of the sample shape data acquired by the shape measurement unit by material and shape of the workpiece and generates the plurality of first learning data sets based on the classified pieces of sample shape data, and the determination model generator generates the determination models for each material and shape of the workpiece using the plurality of second learning data sets.

9. The appearance inspection apparatus of claim 1, wherein the data processor further includes:
    a notification unit configured to notify a result of the determination by the first determination unit.

10. The appearance inspection apparatus of claim 1, wherein the determination models are reinforced in advance by learning using the second learning data sets, each of the first learning data sets and the second learning data sets includes non-defective data which is shape data including no shape defect in the weld and learning data obtained by identifying, in defective data which is shape data including a shape defect in the weld, a type of the shape defect and labelling the shape defect with the type, the first determination unit inputs the sample shape data inputted from the shape data processor to the determination models, and the determination models determine whether the shape defect is present and identify a type, number, and size of the shape defect and a location of the shape defect with respect to the weld to determine whether the shape of the weld satisfies the predetermined criterion based on the results of the determination and the identification.

11. A welding system comprising:

the appearance inspection apparatus of claim 1; and a welding apparatus configured to weld the workpiece, wherein the welding apparatus includes at least:

a welding head configured to apply heat to the workpiece; and an output controller configured to control a welding output of the welding head.

12. The welding system of claim 11, wherein the welding apparatus includes at least:

the robot configured to hold the welding head and move the welding head to a desired position; and a robot controller configured to control a motion of the robot, and when the first determination unit determines that the shape of the weld fails to satisfy the predetermined criterion, the output controller stops the welding output of the welding head, and the robot controller stops the motion of the robot or operates the robot so that the welding head moves to a predetermined initial position.

13. A method for appearance inspection of a weld using the appearance inspection apparatus of claim 1, the method comprising at least:

measuring the three-dimensional shape of the weld by the shape measurement unit moving together with the robot to acquire the sample shape data;

generating the plurality of first learning data sets by the first learning data set generator based on the sample shape data;

generating the plurality of second learning data sets by the second learning data set generator based on the plurality of first learning data sets;

generating the multiple types of determination models for determining whether the shape of the weld satisfies the predetermined criterion by the determination model generator using the plurality of second learning data sets; and determining whether the shape of the weld satisfies the predetermined criterion by the first determination unit based on the sample shape data processed by the shape data processor and the determination models generated by the determination model generator, wherein the determination models used by the first determination unit are generated based on at least one of the second learning data sets having a data density closest to a data density of the sample shape data processed by the shape data processor or at least one of the second learning data sets having a resolution closest to a resolution of the sample shape data corrected by the shape data processor.

14. The method of claim 13, wherein the first learning data set generator generates the plurality of first learning data sets by performing data augmentation on the sample shape data, and the second learning data set generator generates the plurality of second learning data sets by changing a data density or resolution of each of the plurality of first learning data sets in different conversion ratios.

15. The method of claim 13, further comprising:

when the sample shape data acquired by the shape measurement unit is different in resolution from any of the plurality of second learning data sets, correcting the resolution of the sample shape data acquired by the shape measurement unit by the shape data processor to a same value as the resolution of any of the plurality of second learning data sets.

16. The method of claim 15, wherein the shape data processor corrects a value of the sample shape data in a Z direction which is a height direction of the weld based on an X-direction resolution and a Y-direction resolution of the sample shape data, the Y-direction resolution is determined based on a travel speed of the robot and a measurement frequency of the shape measurement unit when the shape measurement unit measures the three-dimensional shape of the weld while the robot travels along the welding line at a constant speed, the Y-direction resolution is determined based on the measurement frequency and the speed control function of the robot when the shape measurement unit measures the three-dimensional shape of the weld while the robot travels at an accelerating speed, a decelerating speed, or both accelerating and decelerating speeds in a predetermined section along the welding line, and the speed control function of the robot is a function dependent on time.

17. The method of claim 13, wherein the determination models are reinforced in advance by learning using the second learning data sets, each of the first learning data sets and the second learning data sets includes:

non-defective data which is shape data including no shape defect in the weld; and learning data obtained by identifying, in defective data which is shape data including a shape defect in the weld, a type of the shape defect and labelling the shape defect with the type, the determining of whether the shape of the weld satisfies the predetermined criterion by the first determination unit includes:

determining whether the shape defect is present based on the sample shape data inputted by the shape data processor and the determination models;

identifying a number and size of the shape defect and a location of the shape defect with respect to the weld; and identifying a type of the shape defect, and the first determination unit determines whether the shape of the weld satisfies the predetermined criterion based on the results of the determination and the identifications.

18. The appearance inspection apparatus of claim 1, wherein the second learning data set generator generates the plurality of second learning data sets by changing a data density or resolution of each of the plurality of first learning data sets in different conversion ratios.

* * * * *